(12) United States Patent
Makriyannis et al.

(10) Patent No.: US 7,741,365 B2
(45) Date of Patent: Jun. 22, 2010

(54) PERIPHERAL CANNABINOID RECEPTOR (CB2) SELECTIVE LIGANDS

(75) Inventors: Alexandros Makriyannis, Watertown, MA (US); Atmaram Khanolkar, Coventry, RI (US)

(73) Assignee: University of Connecticut, Farmington, CT (US)

( * ) Notice: Subject to any disclaimer, the term of this patent is extended or adjusted under 35 U.S.C. 154(b) by 892 days.

(21) Appl. No.: 11/323,560

(22) Filed: Dec. 29, 2005

(65) Prior Publication Data

US 2006/0189610 A1    Aug. 24, 2006

Related U.S. Application Data

(63) Continuation-in-part of application No. 10/110,830, filed as application No. PCT/US00/28818 on Oct. 18, 2000, now Pat. No. 6,995,187.

(60) Provisional application No. 60/160,146, filed on Oct. 18, 1999.

(51) Int. Cl.
 *A61K 31/352* (2006.01)
 *C07D 311/78* (2006.01)
(52) U.S. Cl. ................. 514/455; 549/280
(58) Field of Classification Search .................. 514/455; 549/280
See application file for complete search history.

(56) References Cited

U.S. PATENT DOCUMENTS

| | | | |
|---|---|---|---|
| 3,041,343 A | 6/1962 | Jucker et al. |
| 3,465,024 A | 9/1969 | Brownstein et al. |
| 3,573,327 A | 3/1971 | Miyano |
| 3,577,458 A | 5/1971 | Brownstein et al. |
| 3,656,906 A | 4/1972 | Bullock |
| 3,838,131 A | 9/1974 | Gauthier |
| 3,886,184 A | 5/1975 | Matsumoto et al. |
| 3,897,306 A | 7/1975 | Vidic |
| 3,915,996 A | 10/1975 | Wright |
| 3,928,598 A | 12/1975 | Archer |
| 3,944,673 A | 3/1976 | Archer |
| 3,946,029 A | 3/1976 | Descamps et al. |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan et al. |
| 4,176,233 A | 11/1979 | Archer et al. |
| 4,179,517 A | 12/1979 | Mechoulam et al. |
| 4,188,495 A | 2/1980 | Althuis et al. |
| 4,208,351 A | 6/1980 | Archer et al. |
| 4,278,603 A | 7/1981 | Thakkar et al. |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |
| 4,758,597 A | 7/1988 | Martin et al. |
| 4,812,457 A | 3/1989 | Narumiya |
| 4,876,276 A | 10/1989 | Mechoulam |
| 4,885,295 A | 12/1989 | Bell et al. |
| 5,053,548 A | 10/1991 | Tanaka et al. |
| 5,068,234 A | 11/1991 | D'Ambra et al. |
| 5,147,876 A | 9/1992 | Mizuchi et al. |
| 5,223,510 A | 6/1993 | Gubin et al. |
| 5,284,867 A | 2/1994 | Kloog |
| 5,324,737 A | 6/1994 | D'Ambra et al. |
| 5,434,295 A | 7/1995 | Mechoulam et al. |
| 5,440,052 A | 8/1995 | Makriyannis et al. |
| 5,462,960 A | 10/1995 | Barth et al. |
| 5,489,580 A | 2/1996 | Makriyannis et al. |
| 5,521,215 A | 5/1996 | Mechoulam |
| 5,532,237 A | 7/1996 | Gallant et al. |
| 5,538,993 A | 7/1996 | Mechoulam |
| 5,576,436 A | 11/1996 | McCabe et al. |
| 5,605,906 A | 2/1997 | Lau |
| 5,607,933 A | 3/1997 | D'Ambra et al. |
| 5,618,955 A | 4/1997 | Mechoulam et al. |
| 5,624,941 A | 4/1997 | Barth et al. |
| 5,631,297 A | 5/1997 | Pate et al. |
| 5,635,530 A | 6/1997 | Mechoulam |
| 5,688,825 A | 11/1997 | Makriyannis et al. |
| 5,744,459 A | 4/1998 | Makriyannis et al. |
| 5,747,524 A | 5/1998 | Cullinan et al. |
| 5,804,601 A | 9/1998 | Kato et al. |
| 5,817,651 A | 10/1998 | D'Ambra et al. |
| 5,872,148 A | 2/1999 | Makriyannis et al. |
| 5,874,459 A | 2/1999 | Makriyannis et al. |
| 5,925,628 A | 7/1999 | Lee et al. |
| 5,925,768 A | 7/1999 | Barth et al. |
| 5,932,610 A | 8/1999 | Shohami et al. |
| 5,939,429 A | 8/1999 | Kunos et al. |
| 5,948,777 A | 9/1999 | Bender et al. |
| 6,013,648 A | 1/2000 | Rinaldi et al. |
| 6,028,084 A | 2/2000 | Barth et al. |
| 6,096,740 A | 8/2000 | Mechoulam |
| 6,127,399 A | 10/2000 | Yuan |
| 6,166,066 A | 12/2000 | Makriyannis et al. |
| 6,284,788 B1 | 9/2001 | Mittendorf et al. |

(Continued)

FOREIGN PATENT DOCUMENTS

EP    0276732    8/1988

(Continued)

OTHER PUBLICATIONS

Golub et al. Science (1999), vol. 286 521-537.*

(Continued)

*Primary Examiner*—Kamal A Saeed
*Assistant Examiner*—Samantha L Shterengarts
(74) *Attorney, Agent, or Firm*—Alix, Yale & Ristas, LLP

(57) ABSTRACT

Novel polycyclic cannabinoid analogs are presented which have preferentially high affinities for the cannabinoid CB2 receptor sites.

6 Claims, 13 Drawing Sheets

U.S. PATENT DOCUMENTS

| | | |
|---|---|---|
| 6,391,909 B1 | 5/2002 | Makriyannis et al. |
| 6,579,900 B2 | 6/2003 | Makriyannis et al. |
| 6,610,737 B1 | 8/2003 | Garzon et al. |
| 6,653,304 B2 | 11/2003 | Leftheris et al. |
| 6,864,291 B1 | 3/2005 | Fride et al. |
| 6,900,236 B1 | 5/2005 | Makriyannis et al. |
| 6,903,137 B2 | 6/2005 | Fride et al. |
| 6,939,977 B2 | 9/2005 | Makriyannis et al. |
| 6,943,266 B1 | 9/2005 | Makriyannis et al. |
| 6,995,187 B1 | 2/2006 | Makriyannis et al. |
| 2003/0149082 A1 | 8/2003 | Makriyannis et al. |
| 2004/0077649 A1 | 4/2004 | Makriyannis et al. |
| 2004/0077851 A1 | 4/2004 | Makriyannis et al. |
| 2004/0087590 A1 | 5/2004 | Makriyannis et al. |
| 2004/0192667 A1 | 9/2004 | Makriyannis et al. |
| 2004/0236101 A1 | 11/2004 | Makriyannis et al. |
| 2004/0236116 A1 | 11/2004 | Makriyannis et al. |
| 2005/0020679 A1 | 1/2005 | Makriyannis et al. |
| 2005/0074408 A1 | 4/2005 | Makriyannis et al. |
| 2005/0119234 A1 | 6/2005 | Makriyannis et al. |
| 2005/0137173 A1 | 6/2005 | Makriyannis et al. |
| 2005/0239874 A1 | 10/2005 | Makriyannis et al. |
| 2006/0030563 A1 | 2/2006 | Makriyannis et al. |
| 2006/0100208 A1 | 5/2006 | Makriyannis et al. |

FOREIGN PATENT DOCUMENTS

| | | |
|---|---|---|
| EP | 0444451 | 9/1991 |
| EP | 0471609 | 6/1993 |
| EP | 0576357 | 12/1993 |
| EP | 0737671 | 10/1996 |
| EP | 0860168 | 9/2001 |
| FR | 2240003 | 5/1975 |
| FR | 2735774 | 1/2000 |
| GB | 2027021 A | 2/1980 |
| IL | 1995-113228 | 9/1999 |
| JP | 57098228 | 6/1982 |
| JP | 2304080 | 12/1999 |
| NL | 6509930 | 2/1966 |
| WO | WO 94/12466 | 6/1994 |
| WO | WO 97/00860 | 1/1997 |
| WO | WO 97/21682 | 6/1997 |
| WO | WO 97/45407 | 12/1997 |
| WO | WO 99/57106 | 11/1999 |
| WO | WO 99/57107 | 11/1999 |
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 02/12167 | 2/2002 |
| WO | WO 02/058636 | 8/2002 |
| WO | WO 02/060447 | 8/2002 |
| WO | WO 03/005960 | 1/2003 |
| WO | WO 03/020217 | 3/2003 |
| WO | WO 03/035005 | 5/2003 |
| WO | WO 03/063758 | 8/2003 |
| WO | WO 03/064359 | 8/2003 |
| WO | WO 2004/017920 | 3/2004 |
| WO | PCT/US2005/036524 | 10/2005 |
| WO | PCT/US2006/000720 | 1/2006 |

OTHER PUBLICATIONS

Lala et al. Cancer and Metastasis Reviews (1998), 17(1), 91-106.*
U.S. Appl. No. 09/600,786, filed Nov. 24, 1999, Makriyannis et al (this is the U.S. National Phase of the Int'l Application published as WO 00/32200 enclosed herewith).
U.S. Appl. No. 10/110,865, filed Oct. 18, 2000, Makriyannis et al (this is the U.S. National Phase of the Int'l Application published as WO 01/29007 enclosed herewith).
U.S. Appl. No. 10/110,862, filed Oct. 18, 2000, Makriyannis et al (this is the U.S. National Phase of the Int'l Application published as WO 01/28498 enclosed herewith).
U.S. Appl. No. 11/344,762, filed Dec. 29, 2005, *1* Makriyannis et al.
Abadji V., Lin S., Taha G., Griffin G., Stevenson L.A., Pertwee R.G., Makriyannis A.; "(R)-Methanadamide: a chiral novel anandamide possessing higher potency and metabolic stability"; J. Med. Chem.; 37(12); 1889-1893; Jun. 10, 1994.
*1* Alo, B.I.; Kandil, A.; Patil, P. A.; Sharp, M. J.; Siddiqui, M. A.; and Snieckus, V. Sequential Directed Ortho Metalation-Boronic Acid Cross-Coupling Reactions. A general Regiospecific Route to Oxygenerated Dibenzo[b,d]pyran-6-ones Related to Ellagic Acid, J. Org. Chem. 1991, 56, 3763-3768.
Archer et al; "Cannabinoids, synthesis approaches to 9-ketocannabinoids."; J. Org. Chem.; vol. 42; No. 13; 2277-2284; (1977).
*1* Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).
*1* Barnett-Norris et al; "Exploration of biologically relevant conformations of anandamide, . . . "; J. Med. Chem.; vol. 41; 4861-4872; 1998.
*1* Beak, P.; and Brown, R A., The Tertiary Amide as an Effective Director of Ortho Lithiation, J. Org. Chem. 1982, 47, 34-36.
*1* Belgaonkar et al; "Isocoumarins. XIV. synthesius of 3-benzylisocoumarins and 3-benzyl-1(2H)-isoquinolones."; Indian J. Chem; vol. 13; No. 4; 336-338; 1975 (abstract only).
Beltramo M., Stella N., Calignano A., Lin S. Y., Makriyannis A., Piomelli D; "Functional Role of High-Affinity Anandamide Transport, as Revealed by Selective Inhibition"; Science; vol. 277; 1094-1097; 1997.
Beltramo M., Stella N. Calignano A., Lin S. Y., Makriyannis A., Piomelli D; "Identification and Functional Role of High Affinity Anandamide Transport"; Soc. Neurosci. Abstr. 23:137 (1997). (1 page).
Beltramo M., Piomelli D; "Anandamide Transport Inhibition by the Vanilloide Agonist Olvanil"; Europeean J. of Pharmacology; (1999); 364(1); 75-78 (abstract only).
Berdyshev EV, Cannabinoid receptors and the regulation of immune response. Chem Phys Lipids. Nov. 2000; 108(1-2):169-90.
Berglund et al; "Structural requirements for arachidonylethanolamide interaction with CB1 and CB2 cannabinoid receptors: . . . "; Prostanglandins, leukotrienes ands essential fatty acids; 59(2); 111-118; (1998).
Bodnar, V.N., Lozinskii, M.O., Pel'kis, P.S.; "Synthesis fo 2,5-disubstituted 1,3,4-oxadiazoles and 1,4-dihydro-1,2,4,5-tetrazines"; Ukrainskii Khimicheskii Zhurnal (Russian Edition); 48(12); 1308-1311; 1982 (abstract only).
Bracey, M et al, Structural Adaptations in a Membrane Enzyme That Terminates Endocannabinoid Signaling. Science 2002; 298(5599): 1793-1796.
*1* Brenneisen R, Pgli A, Elsohly MA, Henn V. Spiess Y: The effect of orally and rectally administered Δ9-tetrahydrocannabinol on spasticity, a pilot study with 2 patients. Int. J. Clin Pharmacol Ther. (1996) 34:446-452. (abstract only).
*1* Brotchie JM: Adjuncts to dopamine replacement a pragmatic approach to reducing the problem of dyskinesia in Parkinson's disease. Mov. Disord. (1998)13:871-876. (abstract only).
*1* Brown et al; "Synthesis and hydroboration of (-)-2-phenylapopinene, Comparison of mono(2-phenylapoisopinocampheyl)borane with its 2-methyl and 2-ethyl analogues for the chiral hydroboration of representative alkenes"; J. Org. Chem.; 55(4); 1217-1223; (1990).
*1* Buckley NE, McCoy KI, Mpzey E et al, "Immunomodulation by cannabinoids is absent in mice deficient for the cannabinoid CB2 receptor"; Eur. J Pharmacol (2000) 396:141-149.
*1* Burstein et al; "detection of cannabinoid receptors . . . "; Biochem. Biophys. Res. Commun.; vol. 176(1); 492-497; 1991 (abstract only).

Busch-Peterson et al; "Unsaturated side chain beta-11-hydroxyhexahydrocannabinol analogs"; J. Med. Chem.; 39; 3790-3796; (1996).

*1* Calignano A, La Rana G. Diuffrida A, Piomelli D; "Control of pain initiation by endogenous cannabinoids"; Nature (1998) 394:277-291. (abstract only).

Calignano A., La Rana G., Beltramo, M., Makriyannis A., Piomelli D; "Potentiation of Anandamide Hypotension by the Transport Zinhibitor, AM404"; Eur. J. Pharmacol.; 1997; 337 R1-R2.

Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7-R8.

Campbell FA et al; "Are cannabinoids an effective and safe treatment option In the management of pain? A qualitative systematic review"; BMJ. Jul. 7, 2001;323(7303)13-6.

*1* Charalambous A. et al; "5'-azido Δ8-THC: A Novel Photoaffinity Label for the Cannabinoid Receptor"; J. Med. Chem., 35, 3076-3079 (1992).

*1* Charalambous A. et al; "Pharmacological evaluation of halogenated . . . "; Pharmacol. Biochem. Behav.; vol. 40; No. 3; 509-512; 1991.

*1* Cheng et al; "Relationship Between the Inhibition Constant (Ki) and the concentration of Inhibitor which causes 50% Inhibition (IC50) of an Enzymatic Reaction"; Biochem. Pharmacol., 22, 3099-3102, (1973) (abstract only).

Cherest M., Luscindi X.; "The action of acetyl chloride and of acetic anhydride on the lithium nitronate salt of 2-phenylnitroethane . . . "; Tetrahedron; 42(14); 3825-3840; 1986; in French with English abstract.

Cherest M., Lusinchi X.; "A novel electrophilic N-amidation via electron deficient complexes: action of ferric chloride on N-acetyloxyamides"; Tetrahedron Letters; 30(6); 715-718; 1989.

*1* Colombo G, Agabio R, Diaz G. et al; "Appetite suppression and weight loss after the cannabinoid antagonist SR141716"; Life Sci. (1998) 63-PL13-PL117. (abstract only).

Compton D.R. et al; "Pharmacological Profile of a Series of Bicyclic Cannabinoid Analogs: Classification as Cannabimimetic Agents"; J. Pharmacol. Exp. Ther.; 260; 201-209; 1992. (abstract only).

*1* Compton et al; "Synthesis and pharmacological evaluation of ether and related analogues of delta8-. delta9- and delta9,11-tetrahydrocannabinol"; J. Med. Chem; vol. 34; No. 11; 3310-3316; 1991.

*1* Consroe P, Musty R, Rein J, Tillery W, Pertwee R; "The perceived effects of smoked cannabis on patents with multiple sclerosis"; Eur. Neurol. (1997) 38-44-48. (abstract only).

Coxon et al; "Derivatives of nopinone"; Aust. J. Chem.; 23; 1069-1071; (1970) (abstract only).

*1* Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.

Croce, P. D. et al; "Reactions of Hydrazonoyl Halides with Imidazoles and Benzimidesazoles"; J.C.S. Perkin I; vol. 2; 330-332; (1979).

Croce, P. D. et al; "Reaction of Thiete 1,1-Dioxide with alpha-Chlorobenzalphenylhydrazine and Methyl Phenylhydrazonochloroacetate"; Journal of Heterocyclic Chemistry; vol. 15, No. 3; 515-517; (1978).

D'Ambra et al; "C-attached aminoalkylindoles: potent cannabinoid mimetics"; Bioorg. & Med. Chem. Lett., 1996, 6(1), 17-22.

Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.

*1* DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375-8380.

Desarnaud F., Cadas H., Piomelli D.; "Anandamide amidohydrolase activity In rat brain microsomes"; J. Biol. Chem.; 270; 6030-6035; (1995).

Deutsch D.G. et al; "Fatty acid sulfonyl fluorides inhibit anandamide metabolism and bind to cannabinoid receptor"; Biochem. Biophys. Res. Commun. 231(1); 217-221; 1997; CODEN: BBRCA9; ISSN:0006-291X; XP002040933.

Deutsch D.G., Chin S.A.; "Enzymatic synthesis and degradation of anandamide, a cannabinoid receptor agonist"; Biochemical Pharmacology; 46(5); 791-796; 1993.

*1* Devane, W.A. et al; "Determination and Characterization of a Cannabinoid Receptor in a Rat Brain"; Mol. Pharmacol., 34, 605-613 (1988). (abstract only).

Di Marzo, V., Melck, D., Bisogno, T., DePetrocellis, L.; "Endocannabinoids: endogenous cannabinoid receptor ligands with neuromodulatory action"; Trends Neurosci. (1998) 21:521-528.

*1* Di Marzo, V., Bisogno, T., Melck, D., Ross, R., Brockie, H., Stevenson, L., Pertwee, R., DePetrocellis, L., "Interactions between synthetic vanilloids and the endogenous cannabinoid system"; FEBS Letters; (1998); 437(3); 449-454. (abstract only).

*1* Dodd, P.R. et al, A Rapid Method for Preparing Synaptosomes: Comparison with Alternative Procedures, Brain Res., 226, 107-118 (1981). (abstract only).

*1* Dominiami et al; "Synthesis of 5-(tert-Alkyl)resorcinols"; J. Org. Chem. 42(2); 344-346; (1977).

Drake et al, "classical/nonclassical hybrid cannabinoids"; J. Med. Chem.; vol. 41(19); 3596-3608 (1998).

Edery et al; "Activity of novel aminocannabinoids in baboons"; J. Med. Chem.; 27; 1370-1373 (1984).

Eissenstat et al; "Aminoalkylindoles: structure-activity relationships of novel cannabinoid mimetics"; J. Med. Chem. 1995, vol. 38, No. 16, pp. 3094-3105; XP 000651090.

Fahrenholtz, K. E., Lurie, M. and Kierstead, AR. W.; "The Total Synthesis of dl-Δ9-Tetrahydrocannabinol and Four of Its Isomers"; J. Amer. Chem. Soc. 1967, 89(23), 5934-5941.

*1* Fahrenholtz; "The synthesis of 2 metabolites of (−)-delta eight-tetrahydrocannabinol"; J. Org. Chem.; vol. 37(13); 1972; XP002111824.

Fisera, L., Kovac, J., Lesco, J., Smahovsky, V.; "Furan derivatives. Part CLVI. 1,3-dipolar cycloadditions of heterocycles. V. Reaction of C-acetyl-N-phenylnitrilimine with furan derivatives"; Chemicke Zvesti; 35(1); 93-104 1981 (abstract only).

*1* Fride, E. & Mechoulam, R.; "Pharmacological activity of the cannabinoid receptor agonist, anandamide, a brain constituent"; European Journal of Pharmacology, vol. 231; 313-314; 1993.

Galiegue S et al. ; "Expression of central and peripheral cannabinoid receptors in human immune tissues and leukocyte subpopulations"; Eur J Biochem.; Aug. 15, 1995;232(1):54-61. (abstract only).

*1* Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189-194.

*1* Gold et al; "A comparison of the discriminative stimulus properties of delta9-tetrahydrocannabinol and CP 55,940 in rats and rhesus monkeys"; J. Pharmacol. Exp. Ther.; vol. 262(2); 479-486; 1992.

*1* Green K.; "Marijuana smoking vs. cannabinoids for glaucoma therapy."; Arch. Ophthalmol. (1998) Nov. 116(11); 1433-1437. (abstract only).

Griffin, G., Wray, E. J., Tao, Q., McAllister, S. D., Rorrer, W. K., Aung, M., Martin, B. R., Abood, M. E.; "Evaluation of the cannabinoid CB2 receptor selective antagonist, SR144528: further evidence for cannabinoid CB2 receptor absence in the rat central nervous system"; European Journal of Pharmacology; (1999); vol. 377; 117-125.

*1* Hampson, A.J., Grimaldi M. Axpirod J. Wink D; "Cannabidiol and (−) Δ9 tetrahydrocannabinol are neuroprotective antioxidants"; Proc. Natl Acad Sci. USA (Jul. 1998) 95; 8268-8273.

Hanus et al; "Two new unsaturated fatty acid ethanolamides in brain that bind to the cannabinoid receptor"; Journal of medicinal Chemistry; 36(20); 3032-3034; 1993.

*1* Hargreaves, K. et al; "A new sensitive method for measuring thermal nociception in cutaneous hyperalgesia"; Pain; 32; 77-88; (1988) (abstract only).

*1* *** Hemming M, Yellowlees PM; "Effective treatment of Tourette's syndrome with marijuana"; *J. Psychopharmacol*, (1993) 7:389-391.

*1* Herzberg U, Eliav E, Bennett GJ, Kopin IJ; "The analgesic effects of R(+) WIN 55,212-2 mesylate, a high affinity cannabinoid agonist in a rat model of neuropathic pain"; Neurosci. Letts. (1997) 221; 157-160.

Hillard C. J., Edgemond, W. S., Jarrahian W., Campbell, W. B; "Accumulation of N-Arachidonoylethanolamine (Anandamide) into Cerebellar Granule Cells Occurs via Facilitated Diffusion"; Journal of Neurochemistry; 69; 631-638 (1997).

Horrevoets A.J.G et al; "Inactivation of *Escherichia coli* outer membrane phospholipase A by the affinity label hexadecanesulfonyl fluoride"; Eur. J. Biochem.; 198; 247-253; 1991.

Horrevoets A.J.G et al; "Inactivation of reconstituted *Escherichia coli* outer membrane phospholipase A by membrane-perturbing peptides results in an increased reactivity towards the affinity label hexadecanesulfonyl fluoride"; Eur. J. Biochem.; 198; 255-261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

*1* Howlett et al; "Stereochemical effects of 11-OH-delta 8 tetrahydrocannabinol-dimethylheptyl to inhibit adenylate cyclase and bind to the cannabinoid receptor"; Neuropharmacology; vol. 29(2); 161-165; 1990.

Huffman et al; "3-(1',1'-dimethylbutyl)-deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydocannabinols"; tetrahedron; vol. 51(4); 1017-1032; (1995).

*1* Huffman et al; "Synthesis of 5',11 dihydroxy delta 8 tetrahydrocannabinol"; Tetrahedron, vol. 53(39), pp. 13295-13306 (1997).

*1* Huffman et al; "Synthesis of a tetracyclic, conformationally constrained analogue of delta8-THC"; Bioorganic & Medicinal Chemistry; vol. 6(12); 2281-2288; 1998; XP002123230.

*1* Huffman et al; "Synthesis of both enantiomers of Nabilone from a common intermediate. Enantiodivergent synthesis of cannabinoids"; J. Org. Chem.; 1991, 56, 2081-2086.

Huffman et al; "A Pyridone Analogue of Traditional Cannabinoids. A New Class of Selective Ligands for the CB2 Receptor."; Biorg. Med. Chem.; vol. 9(11), Nov. 2001; 2863-2870. (abstract only).

Jbilo, O., Derocq, J., Segui, M., Le Fur, G., Casellas, P.; "Stimulation of peripheral cannabinoid receptor CB2 induces MCP-1 and IL-8 gene expression in human promyelocytic cell line HL60"; FEBS Letters; (1999); vol. 448; No. 21848; 273-277.

*1* Joy JE, Wagtson SJ, Benson JA; "Marijuana and Medicine Assessing the Science Base"; National Academy Press, Washington, DC, USA (1999). (abstract only).

Kaminski NE; "Regulation of the cAMP cascade, gene expression and immune function by cannabinoid receptors"; J Neuroimmunol. Mar 15, 1998;83(1-2):124-32.

Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515-4519; (1996).

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug. 1998; 19(8):373-81.

Koutek B. et al; "Inhibitors of arachidonyl ethanolamide hydrolysis"; J. Biol. Chem.; 269(37); 22937-40; 1994; CODEN: JBCHA3; ISSN: 0021-9258; XP002040931.

Kumar RN, et al; "Pharmacological actions and therapeutic uses of cannabis and cannabinoids"; Anesthesia, 2001, 56: 1059-1068 (abstract only).

Lan, R et al; "Structure activity relationships of pyrazole derivatives as cannabinoid receptor antagonists"; J. Med. Chem.; vol. 42(4); 769-776; (1999).

Lang, W., Qin, C., Hill, W.A., Lin, S., Khanolkar, A.D., Makriyannis, A.; High-Performance Liquid Chromatographic Determination of Anandamide Amidase Activity in Rat Brain Microsomes; Anal. Biochem; (1996), 238, 40-45 (abstract only).

Lang, W. et al; "Substrate Specificity and Stereoselectivity of Rat Brain Microsomal Anandamide Amidohydrolase"; J. Med. Chem.; vol. 42(5); 896-902; (1999).

*1* Lavalle et al; "Efficient conversion of (1R, 5R)-(+)-alpha-pinene to (1S, 5R)-(–)-nopinene"; J. Org. Chem.; vol. 51(8); 1362-1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

*1* Loev, B., Bender, P. E., Dowalo, F., Macko, E., and Fowler, P.; "Cannabinoids. Structure-Activity Studies Related to 1,2-Dimethylheptyl Derivatives"; J. Med. Chem.; vol. 16(11); 1200-1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

*1* Ludt, R.E. et al; "A comparison of the synthetic utility of n-butyllithium and lithium diisopropylamide in the metalations of N,N-dialkyltouamides"; J. Org. Chem.; 38(9); 1668-1674 (1973).

*** Maccarron M., *Endocannabinoids and their actions. Vitamins and Hormones 2002*;65:225-255.

Mackie K., Devane W.A., Hille B.; "Anandamide, an endogenous cannabinoid, inhibits calcium currents as a partial agonist in N18 neuroblastoma cells"; Mol. Pharmacol; 44; 498-0503 (1993).

*1* Martin et al; "Behavioral, biochemical, and molecular modeling evaluations of cannabinoid analogs"; Pharmacol. Biochem. Behav.; vol. 40(3); 471-478; 1991.

*1* Martyn CN. Illis LS, Thom J.; "Nabilone in the treatment of multiple sclerosis"; Lancet (1995) vol. 345; pp. 579.

*1* Matsumoto et al; "Cannabinoids 1.1-amino-and 1 mercapto-7,8,9,10-tetrahydro-6h-dibenzo[b,d]pyrans"; J. of Med. Chem.; vol. 20(1); 17-24; 1977; XP00211825.

*1* Maurer M, Henn V, Dittrich A, Hofmann A.; "Delta-9-tetrahydrocannabinol shows antispastic and analgesic effects in a single case double-blind trial."; Eur. Arch. Psychiat. Clin. Neurosci. (1990), 240:1-4. (abstract only).

*1* Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 235-244; 1996; XP002111823.

Mechoulam et al; "Stereochemical Requirements for cannabinoid activity"; J. Med. Chem.; 23(10); 1068-1072; (1980).

Mechoulam et al; "Structural Requirements for Binding of Anandamide Type Compounds to the Brain Cannabinoid Receptor"; J. Med. Chem.; 40; 659-667 (1997).

Mechoulam et al; "Synthesis of the individual, pharmacologically distinct, enantiomers of a tetrahydrocannabinol derivative"; Tetrahedron Asymmetry; 1: 315-318; (1990) (abstract only).

*1* Mechoulam et al; "Towards Cannabinoid drugs—Revisited"; Progress in Medicinal Chemistry; 35; 199-243; Jul. 3, 1998.

Melck, D., Bisogno, T., DePetrocellis, L., Chuang, H., Julius, D., Bifulco, M., DiMarzo, V.; "Unsaturated Long-Chain N-Acyl-vanillyl-amides"; Biochemical and Biophysical Res. Commun.; (1999); 262(1); 275-284 (abstract only).

*1* Meltzer et al; "An improved synthesis of cannabinol and cannabiorcol"; Synthesis; 1981:985 (1981).

Melvin et al; "Structure-Activity Relationships Defining the ACD-Tricyclic Cannabinoids Cannabinoid Receptor Binding and Analgesic Activity"; Drug Design and Discovery; 13(2); 155-166 (1995). (abstract only).

Melvin et al; "Structure-activity relationships for cannabinoid receptor-binding and analgesic activity: studies of bicyclic cannabinoid analogs"; Mol. Pharmacol.; 44(5); 1008-1015 (1993) (abstract only).

*1* Merck Index; 11th edition; "Tetrahydrocannabinols" compound No. 9142; 1989.

Meschler, J. P., Kraichely, D. M., Wilken, G. H., Howlett, A. C.; "Inverse Agonist Properties of N-(Piperidin-1-yl)-5-(4-chlorophenyl)-1-(2,4-dichlorophenyl)-4-methyl-1H-pyrazole-3-carboxamide HCL (SR141716A) and 1-(2-Chlorophenyl)-4-cyano-5-(4-methoxyphenyl)-1H-pyrazole-3-carboxylic Acid Phenylamide (CP-272871) for the CB1 Cannabinoid Receptor"; Biochemical Pharmacology; (2000); vol. 60; No. 9; 1315-1322.

Molteni, G. et al; "Nitrilimine Cycloadditions in Aqueous Media"; J.C.S. Perkins I; vol. 22; 3742-3745; (2000).

*1* Muller-Vahl KB, Kolbe H, Schneider U, Emrich, HM Cannabis in movement disorders. Porsch. Kompicmentarmed (1999) 6 (suppl. 3) 23-27. (abstract only).

*1* Muller-Vahl KB, Schneider U, Kolbe H, Emrich, HM.; "Treatment of Tourette's syndrome with delta-9-tetrahydrocannabinol." Am. J. Psychiat.; (1999); 156(3); 495.

Neunhoeffer O., Gottschlich R.; "Acylating activity of O-acylated hydroxylamine derivatives"; Justus Liebigs Ann. Chem.; 736; 100-109; 1970; in German with English abstract.

Ng et al; "Unique Analogues of Anandamide: Arachidonyl Ethers and Carbamates and Norarachidonyl Carbamates and Ureas"; J. Med. Chem.; 1999; 42(11); 1975-1981.

*1* Novak, J et al; Cannabis, part 27, synthesis of 8-, 10- and 11-oxygenated cannabinoids; J. Chem. Soc. Perkin Trans.; 2867-2871; (1983) (abstract only).

*1* Nye et al; "High affinity cannabinoid binding sites in brain membranes labelled with [H]-5' -trimethylammonium delta8-tetrahydrocannabinol"; J. Pharmacol. Exp. Ther.; vol. 234(3); 784-791; 1985.

Pacheco M, et al; "Aminoalkylindoles: Actions on Specific G-Protein-Linked Receptors"; J. Pharmacol. Exp. Ther.; vol. 257, No. 1, pp. 170-183 (1991).

Palmer et al; "Natural and Synthetic Endocannabinoids and Their Structure-Activity Relationships"; Current Pharmaceutical Design; 6; 1381-1397; (2000).

*1* Papahatjis et al; "A new ring-forming methodology for the synthesis of conformationally constrained bioactive molecules"; Chemistry Letters, 192; (2001).

*1* Papahatjis et al; "Pharmacophoric requirements for cannabinoid side chains: multiple bond and C1'-substituted delta8-tetrahydrocannabinols"; J. Med. Chem.; 41(7); 1195-1200; (1998).

Pertwee et al; "AM630, a competitive cannabinoid receptor agonist"; Life Sci. 1995, 56(23/24), 1949-1955; XP 000653566.

Pertwee et al; "Pharmacological characterization of three novel cannabinoid receptor agonists in the mouse isolated vas deferens"; Eur. J. Pharmacol. 1995, 284, 241-247; XP-001041044.

Pertwee et al; "Inhibitory effects of certain enantiomeric cannabinoids in the mouse vas deferens and the myenteric plexus preparation of guinea-pig small intestine"; Br. J. Pharmacol.; 105(4); 980-984 (1992). (abstract only).

*1* Pertwee; Pharmacology of cannabinoid CB1 and CB2 receptors; Pharmacol. Ther., vol. 74(2); pp129-180; (1997); XP002226467.

Petrov, M.L., Terent'eva, N. A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-Phenylnitrilimine"; Zhurnal Organicheskoi Khimii; 29(7); 1372-1378; (1993) (abstract only).

Pinto et al; Cannabinoid Receptor Binding and Agonist Activity of Amides and Esters of Arachidonic Acid; Mol. Pharmacol.; 1994; 46(3); 516-522.

Piomelli D., Beltramo M., Glasnapp S., Lin S.Y., Goutopoulos A., Xiw X-Q., Makriyannis A.; "Structural determinants for recognition and translocation by the anandamide transporter"; Proc. Natl. Acad. Sci. USA; 96; 5802-5807; (1999).

*1* Pitt et al; "The synthesis of Deuterium, carbon-14 and carrier free tritium labelled cannabinoids"; Journal of Labellled Compounds; vol. 11(4); 551-575; 1975; XP002123229.

Porreca F., Mosberg H.I., Hurst R., Hruby V.J., Burks T.F.; "Roles of mu, delta and kappa opiod receptors in spinal and supraspinal mediation of gastrointestinal transit effects and hot-plate analgesia in the mouse"; J. Pharmacol. Exp. Ther.; 230(2); 341-348; (1994). (abstract only).

Quere, L., Boigegrain, R., Jeanjean, F., Gully, D., Evrard, G., Durant, F.; "Structural requirements of non-peptide neurotensin receptor antagonists"; J. Chem Soc., Perkin Trans. 2, (1996); 2639-2646.

Razdan et al; "Drugs derived from cannabinoids. 6. .Synthesis of cyclic analogues of dimethylheptylpyran"; J. Med. Chem.; vol. 19(5); 719-721; 1976 (abstract only).

*1* Razdan et al; "Pharmacological and Behavioral Evaluation of Alkylated Anandamide Analogs"; Life Sci.; 1995; 56(23-24); 2041-2048.

*1* Reggio et al; "Characterization of a region of steric interference at the cannabinoid receptor using the active analog approach"; J. Med. Chem. United States; vol. 36(12); 1761-1771; 1993.

*1* Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228-3233.

Rice AS. Cannabinoids and pain. Curr Opin Investig Drugs. Mar. 2001;2(3):399-414. (abstract only).

*1* Richardson JD, Aanonsen I, Hargreaves KM; "Antihyperalgesic effects of a spinal cannabinoids"; Eur. J. Pharmacol. (1998) 346:145-153.

*1* Richardson JD, Kilo S. Hargreaves KM; "Cannabinoids reduce dryperalgesia and inflammation via interaction with peripheral CB1 receptors"; Pain (1998) 75:111-119.

Rinaldi-Carmona et al; "Biochemical and pharmacological characterization of SR141716A, the first potent and selective brain cannabinoid receptor antagonist"; Life Sci.; vol. 56(23/24); 1941-1947 (1995).

Rinaldi-Carmona et al; "SR141716A, a potent and selective antagonist of the brain cannabinoid receptor"; FEBS Lett.; 350; 240-244; (1994).

*1* Rompp Chemie Lexikon; Falbe and Regitz; "band 1-A-C1, 8"; Aufl, Thieme Verlag; Stuttgart, S 569-570; 1989.

Santus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278-87.

*1* *** Schuel, H., Burkman, L.J., Picone, R.P., Bo, T., Makriyannis, A., Cannabinoid receptors in human sperm. *Mol. Biol. Cell.*, (1997) (8), 325a.

Serdarevich B., Caroll K.K., "Synthesis and characterization of 1- and 2-monoglycerides of anteiso fatty acids"; J. Lipid Res.; 7; 277-284; (1966).

Shawali, A.S., Albar, H.A.; "Kinetics and mechanism of dehydrochlorination of N-aryl-C-ethoxycarbonyl formohydrazidoyl chlorides"; Canadian Journal of Chemistry; 64(5); 871-875; 1986 (abstract only).

*1* Shen M. Thayer SA: Cannabinoid receptor agonists protect cultured rat hippocampal neurons from excitotoxicity. Mol. Pharmacol (1996) 54:459-462.

Sheskin, T. et al; Structural Requirements for Binding of Anandamide Type Compounds to the Brain Cannabinoid Receptor; J. Med. Chem.; 1997; 40; 659-667.

Shim et al; "Three-dimensional quantitative structure-activity relationship study of the cannabimimetic (aminoalkyl)indoles using comparative molecular field analysis"; J. Med. Chem.; 1998, 41(23); 4521-4532; XP-002212407.

Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.

Shiue, J-S et al; "Phenyl-Carbonyl Coupling Reactions Promoted by Samarium Diiodide and Hexamethylphosphoramide"; J. Org. Chem.; vol. 62, No. 14; 4643-4649; (1997).

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.

*1* Simiand J, Keane M, Keane PE, Soubrie P: SR 141716, A CB1 cannabinoid receptor antagonist, selectively reduces sweet food intake in marmoset. Behav. Pharmacol (1998) 9:179-181. (abstract only).

*1* Smith P.B. et al; "The pharmacological activity of anandamide, a putative endogenous cannabinoid, in mice"; Journal of Pharmacology and Experimental Therapeutics; vol. 270(1):219-227; 1994.

*1* Terranova J-P, Storme J-J Lafon N et al; "Improvement of memory in rodents by the selective CB1 cannabinoid receptor antagonist, SR 141716"; Psycho-pharmacol (1996) 126:165-172 (abstract only).

Tetko, I. V. et al; "Volume Learning Algoritm Artificial Neural Networks for 3D QSAR Studies"; J. Med. Chem.; vol. 44, No. 15 (2001) pp. 2411-2420.

Tewari, R. S. et al; "1,3-Dipolar Cycloadditions and Nucleophilic Substitution Reactions of C-Acetyl and C-Ethoxycarbonyl Derivative of Hydrazidoyl Bromides"; Tetrahedron; vol. 39, No. 1; 129-136; (1983).

Tius et al; "Conformationally restricted hybrids of CP-55,940 and HHC: Steroeselective synthesis and activity"; Tetrahedron; 50 (9); 2671-2680; (1994) (abstract only).

Twitchell, W. et al; "Cannabinoids inhibit N- and P/Q type calcium channels in cultured rat hippocampal neurons"; Journal of Neurophysiology; 78(1); 43-50; 1997 (abstract only).

Ueda, N., Endocannabinoid hydrolases. Prostaglandins & Other Lipid Mediators 2002;68-69:521-534 (abstract only).

Vogel Z., Barg J., Levy R., Saya D., Heldman E., Mechoulam R.; "Anandamide, a brain endogenous compound, interacts specifically with cannabinoid receptors and inhibits adenylate cyclase"; J. Neurochem.; 61(1) 352-355; (1993) (abstract only).

*1* Wagner JA, Varga K, Jarai Z, Kunos G; "Mesenteric Vasodilation Mediated by Endothelia Anandamide Receptors"; Hypertension (1999) 33:429-434.

*1* Watanabe, T.; Miyaura, N.; and Suzuki, A.; "Synthesis of Sterically Hindered Biaryls via the Palladium Catalyzed Cross-Coupling Reaction of Arylboronic Acids or their Esters with Haloarenes"; Synlett 1992, 207-210.

Wiley et al; "Structure activity relationships of indole and pyrrole derived cannabinoids"; J. Pharmacol. Exp. Ther. 1998, 285(3), 995-1004; XP-001097982.

Wilson et al; "9-nor-delta8-tetrahydrocannabinol, a cannabinoid of metabolic intersts"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydrohexahydrocannabinols. Synthesis, some behavioral and analgesic properties, and comparison with the tetrahydrocannabinols"; J. Med. Chem.; 19(9); 1165-1167; (1976).

Yamada et al; "(Aminoalkyl)indole isothiocyanates as potentiual electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1' -dimethylheptyl)hexahydrocannabinol: a high affinity cannabinoid agonist"; J. Med. Chem.; vol. 37(16); 2619-2622; (1994).

*1* Yan Guo et al; "(−)-11-hydroxy-7'-isothiocyanato-1'-1'dimethylheptyl-delta8-THC: a novel probe for the cannabinoid receptor in the brain"; J. Med. Chem.; 37(23); 3867-3870; (1994).

Ibrahim et al.; "Activation of CB2 cannabinoid receptors by AM1241 inhibits experimental neuropathic pain: Pain inhibition by receptors not present in the CNS"; PNAS; 100(18); pp. 10529-10533; Sep. 2, 2003. ("PNAS 100").

Quartilho et al.: "Inhibition of Inflammatory Hyperalgesia by Activation of Peripheral CB2 Cannabinoid Receptors"; Anesthesiology; 99(4); pp. 955-960; Oct. 2003. ("Anesthesiology 99").

Ibrahim et al.; "CB2 cannabinoid receptor activation produces antinociception by stimulating peripheral release of endogenous opioids"; PNAS; 102(8); pp. 3093-3098; Feb. 22, 2005. ("PNAS 102").

Nackley et al.; "Activation of Cannabinoid Receptors Suppresses C-Fiber Responses and Windup in Spinal Wide Dynamic Range Neurons in the Absence of presence of Inflammation"; J. Neurophysiol; 92; pp. 3562-3574; 2004. ("J. Neurophysiol 92").

Lu, D., Vemuri, V. K., Duclos, R. I., Jr.; Makriyannis, A. The cannabinergic system as a target for anti-inflammatory therapies. Curr Top Med Chem 6, (13), 1401-26. ("Current Topics 6").

Rahn et al.: "Activation of cannabinoid CB1 and CB2 receptors suppresses neuropathic nociception evoked by the chemotherapeutic agent vincristine in rats"; British Journal of Pharmacology; pp. 1-13; 2007. ("British Journal of Pharmacology 2007").

Ibrahim et al.; "CB2 cannabinoid receptor mediation of antinociception"; Pain; 122; pp. 36-42; 2006. ("Pain 122").

Sickle et al.; "Identification and Functional Characterization of Brainstem Cannabinoid CB2 Receptors"; Science; 310; pp. 329-332; 2005. ("Science 310").

Gutierrez, T., Farthing, J. N., Zvonok, A. M., Makriyannis, A.; Hohmann, A. G. Activation of peripheral cannabinoid CB1 and CB2 receptors suppresses the maintenance of inflammatory nociception: a comparative analysis. Br. J. Pharmacol. 150, (2), 153-163. ("British Journal of Pharmacology 150").

Kim, K., Moore, D. H., Makriyannis, A.; Abood, M. E. AM1241, a cannabinoid CB2 receptor selective compound, delays disease progression in a mouse model of amyotrophic lateral sclerosis. Eur. J. Pharmacol. 542, (1-3), 100-105. ("European Journal of Pharmacology 542").

Nackley, A. G., Makriyannis, A.; Hohmann, A. G. Selective activation of cannabinoid CB2 receptors suppresses spinal fos protein expression and pain behavior in a rat model of inflammation. Neuroscience (Oxford, U. K.) 119, (3), 747-757. ("Neuroscience 119").

Marchalant, Y, Rosi, S.; Wenk, G. L. Anti-inflammatory property of the cannabinoid agonist WIN-55212-2 in a rodent model of chronic brain inflammation. Neuroscience 144, (4), 1516-22 ("Neuroscience 144").

Shoemaker, J. L., Seely, K. A., Reed, R. L., Crow, J. P.; Prather, P. L. The CB2 cannabinoid agonist AM-1241 prolongs survival in a transgenic mouse model of amyotrophic lateral sclerosis when initiated at symptom onset. J. Neurochem. 101, (1), 87-98. ("Journal Neurochem 101").

Ashton, J. C.; Glass, M. The Cannabinoid CB2 Receptor as a Target for Inflammation-Dependent Neurodegeneration. Curr Neuropharmacol 5, (2), 73-80. ("Current Neuropharmacol 5").

Benito, C., Tolon, R. M., Pazos, M. R., Nunez, E., Castillo, A. I.; Romero, J. Cannabinoid CB2 receptors in human brain inflammation. Br J Pharmacol 153, (2), 277-85. ("British Journal of Pharmacology 153").

Fernandez-Ruiz, J., Pazos, M. R., Garcia-Arencibia, M., Sagredo, O.; Ramos, J. A. Role of CB2 receptors in neuroprotective effects of annnabinoids. Mol Cell Endocrinol 286, (1-2 Suppl 1), S91-6. ("Molecular Cell 286").

* cited by examiner

300μg AM251 (A SELECTIVE CB1 ANTAGONIST) ADMINISTERED IN THE HINDPAW DID NOT BLOCK THE ANALGESIC EFFECTS OF INTRAPLANTAR 1000μg AM1714

300μg INTRAPLANTAR AM251 DID NOT BLOCK THE ANALGESIC EFFECTS OF 300μg I.P ADMINISTERED AMI714 IN NAIVE RATS

PERIPHERAL CANNABINOID RECEPTOR (CB2) SELECTIVE LIGANDS

RELATED APPLICATIONS

The present application is a continuation-in-part of U.S. application Ser. No. 10/110,830, filed Oct. 21, 2002 now U.S. Pat. No. 6,995,187, which was the U.S. National Stage of International Application No. PCT/US/00/28818, filed Oct. 18, 2000, which claims the benefit of U.S. Provisional Application No. 60/160,146, filed Oct. 18, 1999, the contents of each of which are incorporated herein by reference in their entirety.

FIELD OF THE INVENTION

The present invention relates generally to cannabinoid compounds and is more particularly concerned with new and improved cannabinoid compounds exhibiting high binding affinities for the CB2 cannabinoid receptor, pharmaceutical preparations employing these analogs and methods of administering therapeutically effective amounts of the preparations to provide a physiological effect.

BACKGROUND OF THE INVENTION

Classical cannabinoids such as the marijuana derived cannabinoid $\Delta^9$-tetrahydrocannabinol, ($\Delta^9$-THC) produce their pharmacological effects through interaction with specific cannabinoid receptors in the body. So far, two cannabinoid receptors have been characterized: CB1, a central receptor found in the mammalian brain and peripheral tissues and CB2, a peripheral receptor found only in the peripheral tissues. Compounds that are agonists or antagonists for one or both of these receptors have been shown to provide a variety of pharmacological effects. See, for example, Pertwee, R. G., *Pharmacology of cannabinoid CB1 and CB2 receptors*, Pharmacol. Ther., (1997) 74:129-180 and Di Marzo, V., Melck, D., Bisogno, T., DePetrocellis, L., *Endocannabinoids: endogenous cannabinoid receptor ligands with neuromodulatory action*, Trends Neurosci. (1998) 21:521-528.

There is considerable interest in developing cannabinoid analogs possessing high affinity for the CB2 receptor. Cannabinoid analogs that preferentially stimulate the CB2 receptor, directly or indirectly, can provide clinically useful effects without affecting the subject's central nervous system. Such analogs may offer a rational therapeutic approach to a variety of disease states.

SUMMARY OF THE INVENTION

It has now been found that certain novel cannabinoids possess improved CB2 receptor affinity over known cannabinoids. In one aspect of the invention, novel cannabinoids can be represented by the following formula and physiologically acceptable salts thereof.

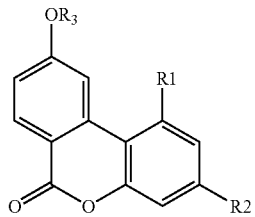

and physiologically acceptable salts thereof, wherein $R_1$ is selected from OH; H; $OCH_3$; $N_3$; $NH_2$; $O(CH_2)_nN(CH_3)_2$ and

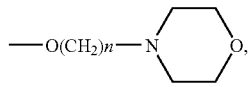

where n is an integer from 1-3.

$R_2$ is selected from $(CH_2)_nCH_3$, where n is an integer from 4-6;

$C(CH_3)_2(CH_2)_nCH_3$, where n is an integer from 3-5;

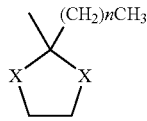

where each X is independently selected from $CH_2$, O, S and NH and n is an integer from 3-5;

$(CH_2)_nC\equiv CH$ where n is an integer from about 3-5;

$C\equiv C(CH_2)_nCH_3$ where n is an integer from 2-4 and

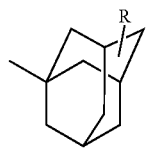

where R is H, $(CH_2)_nCH_3$, and n is a maximum of 7.

$R_3$ is selected from H; $CH_3$; $C_2H_5$; $C_3H_7$; $C_4H_9$; $(CH_2)_nN(CH_3)_2$ and

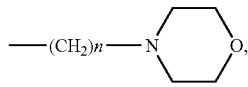

where n is an integer from 1-3.

The novel cannabinoids are also more polar (less lipophilic) then known cannabinoids, which can improve their therapeutic usefulness in certain applications. Therefore, the novel cannabinoids described herein, and physiologically acceptable salts thereof, represent potentially useful materials for providing a physiological effect to treat pain, peripheral pain, glaucoma, epilepsy, nausea such as associated with cancer chemotherapy, cancer, neurodegenerative diseases including Multiple Sclerosis, Parkinson's Disease, Huntington's Chorea and Alzheimer's Disease, to reduce fertility; to prevent or reduce diseases associated with motor function such as Tourette's syndrome; to prevent or reduce inflammation; to provide neuroprotection and to modulate the immune system. Thus, another aspect of the invention is the administration of a therapeutically effective amount of an inventive compound, or a physiologically acceptable salt thereof, to an individual or animal to provide a physiological effect.

DESCRIPTION OF SOME PREFERRED EMBODIMENTS

Figure 1:
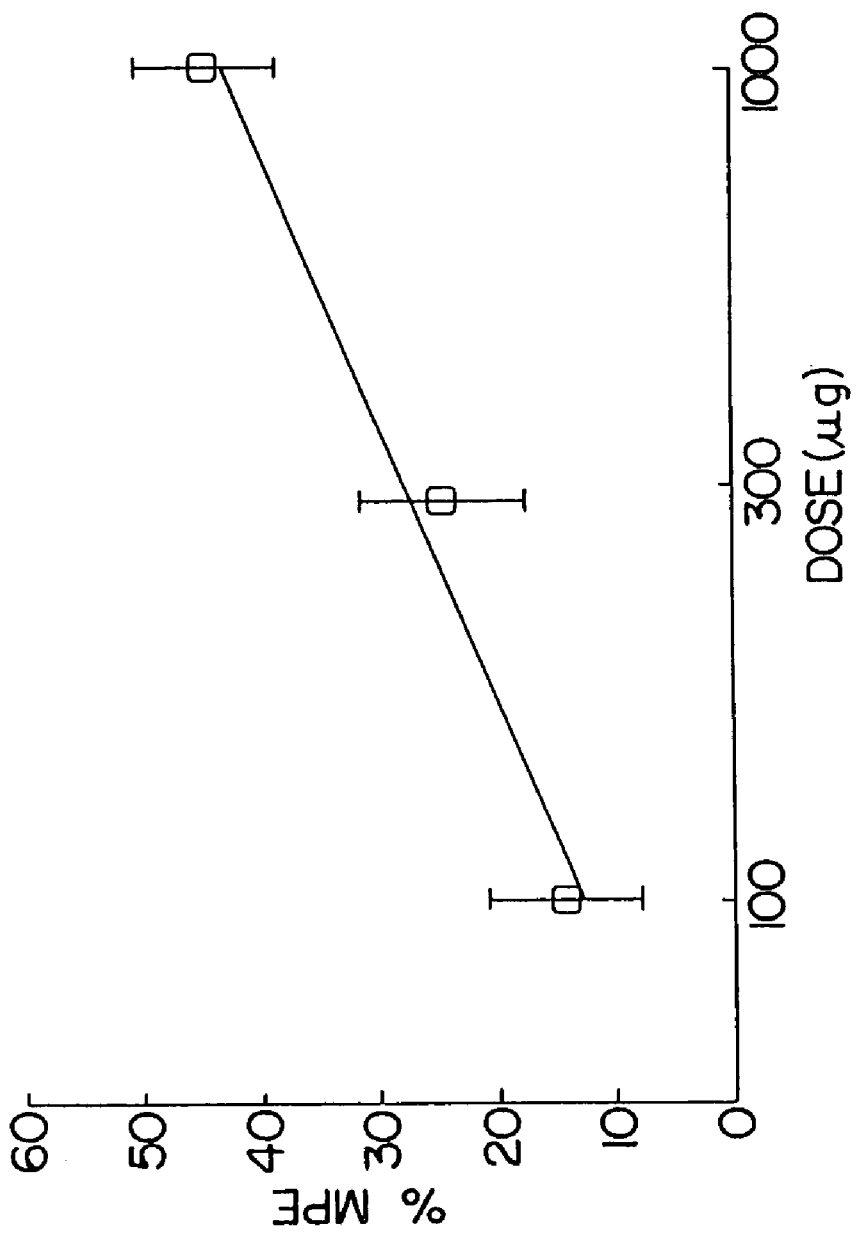
FIGS. 1-13 are graphs illustrating the physiological effects of the novel cannabinoid compounds.

As used herein a "therapeutically effective amount" of a compound, is the quantity of a compound which, when administered to an individual or animal, results in a sufficiently high level of that compound in the individual or animal to cause a discernible increase or decrease in stimulation of cannabinoid receptors. Physiological effects that result from cannabinoid receptor stimulation include analgesia, decreased nausea resulting from chemotherapy, sedation and increased appetite. Other physiological functions include relieving intraocular pressure in glaucoma patients and suppression of the immune system. Typically, a "therapeutically effective amount" of the compound ranges from about 10 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically to acceptable vehicles may include, for example, saline, sterile water, Ringer's solution, and isotonic sodium chloride solutions. The specific dosage level of active ingredient will depend upon a number of factors, including, for example, biological activity of the particular preparation, age, body weight, sex and general health of the individual being treated.

The inventive compounds can generally be described with reference to the below formula and include physiologically acceptable salts thereof.

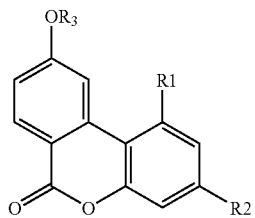

and physiologically acceptable salts thereof, wherein $R_1$ is selected from OH; H; $OCH_3$; $N_3$; $NH_2$; $O(CH_2)_nN(CH_3)_2$ and

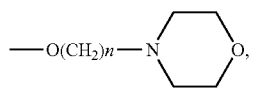

where n is an integer from 1-3.

$R_2$ is selected from $(CH_2)_nCH_3$, where n is an integer from 4-6;
$C(CH_3)_2(CH_2)_nCH_3$, where n is an integer from 3-5;

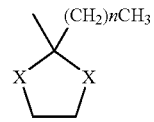

where each X is independently selected from $CH_2$, O, S and NH and n is an integer from 3-5;
$(CH_2)_nC{\equiv}CH$ where n is an integer from about 3-5;
$C{\equiv}C(CH_2)_nCH_3$ where n is an integer from 2-4 and

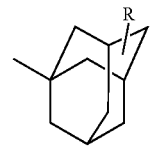

where R is H, $(CH_2)_nCH_3$, and n is a maximum of 7.

$R_3$ is selected from H; $CH_3$; $C_2H_5$; $C_3H_7$; $C_4H_9$; $(CH_2)_nN(CH_3)_2$ and

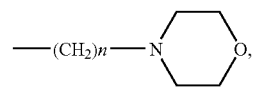

where n is an integer from 1-3.

The following examples are given for purposes of illustration only in order that the present invention may be more fully understood. These examples are not intended to limit in any way the practice of the invention. The preparation procedures include aspects of the following references, the disclosures of which are hereby incorporated by reference. Alo, B. I.; Kandil, A.; Patil, P. A.; Sharp, M. J.; Siddiqui, M. A.; and Snieckus, V. *Sequential Directed Ortho Metalation-Boronic Acid Cross-Coupling Reactions. A General Regiospecific Route to Oxygenated Dibenzo[b,d]pyran-6-ones Related to Ellagic Acid*, J. Org. Chem. 1991, 56, 3763-3768. Beak, P.; and Brown, R. A., *The Tertiary Amide as an Effective Director of Ortho Lithiation*, J. Org. Chem. 1982, 47, 34-46. Watanabe, T.; and Miyaura; Suzuki, A., *Synthesis of Sterically Hindered Biaryls via the Palladium Catalyzed Cross-Coupling Reaction of Arylboronic Acids or their Esters with Haloarenes*, Synlett 1992, 207-210. Morris, S.; Mechoulam, R.; and Irene, Y., *Halogenation of Phenols and Phenyl Ethers with Potassium Halides in the Presence of 18-Crown-6 on Oxidation with m-Chloroperbenzoic Acid*, J. Chem. Soc., Perkin Trans. 1 1987, 1423-1427. Rhee, M. H.; Vogel, Z.; Barg, J.; Bayewitch, M.; Levy, R.; Hanus, L.; Breuer, A.; and Mechoulam, R., *Cannabinol Derivatives: Binding to Cannabinoid Receptors and Inhibition of Adenylylcyclase*, J. Med. Chem. 1997, 40, 3228-3233. Ludt, R. E.; Griffiths, J. S.; McGrath, K. N.; and Hauser, C. R., *Metalations of N,N-Dialkyltouamides, J. Org. Chem.* 1973, 38, 1668-1674. Novak, J.; and Salemink, C. A., *Cannabis. Part 27. Synthesis of 8-, 10-, and 11-Oxygenated Cannabinoids, J. Chem. Soc. Perkin Trans.* 1983, 2867-2871. Materials AM1710 and AM1714 were prepared.

Material AM1710 can be represented by the above structural formula when $R_1$ is OH, $R_2$ is 1,1-dimethylheptyl and $R_3$ is $CH_3$. Material AM1714 can be represented by the above structural formula when $R_1$ and $R_3$ are each OH and $R_2$ is 1,1-dimethylheptyl. Materials AM1710 and AM1714 were prepared as follows.

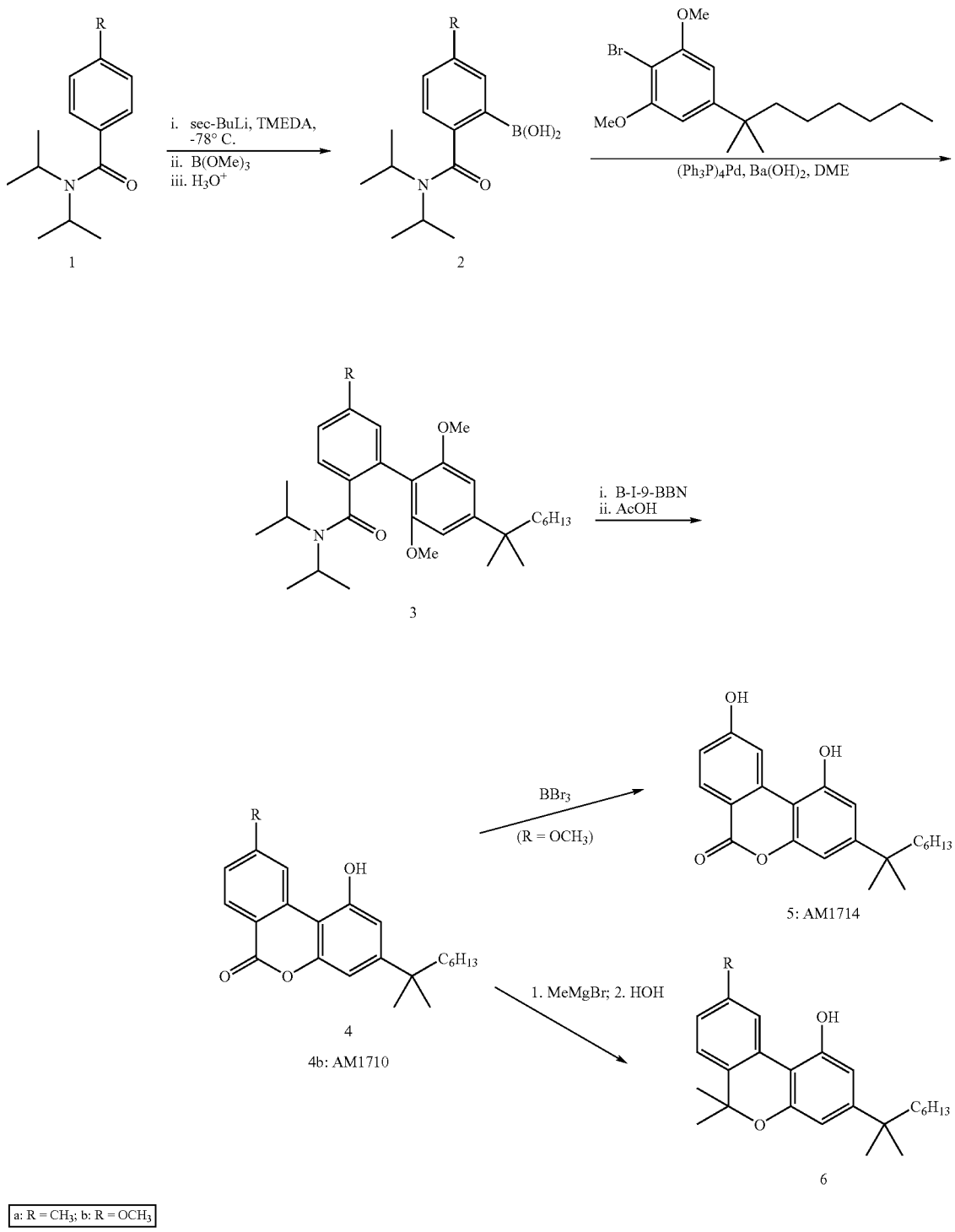

Scheme 1

General. Proton NMR spectra were recorded on Bruker 200 MHz and 500 MHz spectrometers as solutions in deuterated chloroform unless noted otherwise. Routine GC-MS analyses of the intermediates and the final products were performed on a Hewlett-Packard 6890A series gas chromatograph coupled with a mass selective detector (MSD). Tetrahydrofuran (THF) was distilled from sodium-benzophenone ketyl immediately prior to the use. Anhydrous ethylene glycol dimethyl ether (dimethoxyethane) was purchased from Aldrich Chemical Company and degassed using argon for the Suzuki biphenyl coupling reaction. Trimethylborate, tetrakis (triphenylphosphine)palladium, barium hydroxide octahydrate, boron tribromide, and B-iodo-9-BBN were also purchased from Aldrich Chemical Company. Purification by flash chromatography was carried out on silica gel, grade 9385 (230-400 mesh) using solvents indicated in the parenthesis as eluents. Thin layer chromatographic analyses were carried out Whatman 60$F_{254}$ polyester plates.

2-(N,N-Diisopropylcarboxamido)-5-methoxyphenylboronic acid (2b). Anhydrous tetrahydrofuran (210 mL) and TMEDA (8.52 mL, 56.6 mmol) was cooled to −78° C. under argon and, with stirring, 43.2 mL of a 1.3 M sec-butyllithium (56.2 mmol) solution was added via syringe. The yellow solution was stirred at the same temperature for about 5 min and a solution of 12 g (51.1 mmol) of 4-methoxy-N,N-diisopropylbenzamide in 36 mL of anhydrous THF was added in a dropwise manner. The yellow color became more intense. The reaction mixture was stirred at −78° C. for 45 min and then 17.2 mL (153.5 mmol) of trimethylborate was added when the yellow color disappeared. The mixture was allowed to warm to room temperature overnight. The pH of the mixture was adjusted to about 6.5 by addition of 5% aqueous hydrochloric acid (about 50 mL) and concentrated on a rotary evaporator. The residue was extracted with dichloromethane. The combined organic extracts were dried and solvent removed to afford a yellow foam in vacuo which settled to a thick viscous product. Purity of the boronic acid was checked by TLC analysis and it was used as such in the Suzuki coupling reaction.

N,N-Diisopropyl-5,1',6'-trimethoxy-4'-(1,1-dimethyl) heptyl-2-biphenylcarboxamide (3b). The above boronic acid (2.41 g, 8.68 mmol, 1.1 equiv.), tetrakistriphenylphosphine palladium (546 mg, 0.47 mmol, 0.06 equiv.) and barium hydroxide octahydrate (3.72 g, 11.81 mmol, 1.5 equiv.) and dimethoxyethane (40 mL) were combined; 7.9 mL of water was added and the reaction mixture was stirred at room temperature, under argon, for 5 min. Then, a solution of 2.41 g (7.87 mmol) of the aryl bromide in 7 mL of dimethoxyethane was added with stirring and the mixture was stirred and refluxed under argon for 24 hours (h). After cooling to room temperature, the catalyst was filtered off through celite and the filtrate was concentrated on the rotary evaporator. The residue was chromatographed on silica gel (20-50% diethyl ether-petroleum ether) to afford 2.00 g (52% yield based on the amide) of the desired biphenyl. Also, 1.25 g of the aryl bromide was recovered. The yield of the biphenyl based on the recovered bromide was 94%. $R_f$: 0.28 (50% diethyl ether-petroleum ether); $^1$H NMR (CDCl$_3$) δ 7.28 (m, 1H), 6.75 (m, 2H), 6.49 (s, 1H), 3.80 (s, 3H), 3.72 (s, 6H), 3.52 (m, 1H), 3.15 (m, 1H), 1.50-0.90 (complex m, 11H), 1.45 (d, 3H), 1.28 (s, 6H), 1.05 (d, 3H), 0.84 (overlapping pattern, 6H), 0.52 (d, 3H). HRMS Calcd for $C_{31}H_{47}NO_4$ 497.7092. Found 497.7095.

3-(1,1-Dimethylheptyl)-1-hydroxy-9-methoxy-6H-dibenzo[b,d]pyran-6-one (4b). The biphenyl intermediate (500 mg, 1 mmol) was dissolved in 10 mL of dry dichloromethane and 4 mL of a 1 M solution of B-I-9-BBN (4 mmol) in hexanes was added via syringe. The reaction mixture was stirred at room temperature for 4 h. Then, most of the dichloromethane was removed and the residue was dissolved in diethyl ether and 0.24 mL of ethanolamine was added. The mixture was allowed to stir at room temperature for 2 h; the precipitate was filtered off and the filtrate was concentrated. The residue was dissolved in 5 mL of glacial acetic acid and refluxed for 5 h. The solution was cooled to room temperature, diluted with water and extracted with diethyl ether. The ether extract was dried and ether evaporated. TLC of the residue indicated only one product which was purified by chromatography on silica gel (50% diethyl ether-petroleum ether) to afford 272 mg of a white solid. It was not the expected 1,9-dihydroxy product but rather had a methoxy group at C-9 position as seen by proton NMR spectroscopy. The structure was confirmed by x-ray crystallography: m.p. 149-151° C.; $R_f$: 0.44 (50% diethyl ether-petroleum ether); $^1$H NMR δ 8.51 (m, 1H), 8.35 (d, 1H), 7.03 (m, 1H), 6.90 (s, 1H), 6.73 (s, 1H), 6.57 (s, 1H), 3.95 (s, 3H), 2.01-0.95 (series of m, 10H), 1.26 (s, 6H), 0.81 (t, J=6.6 Hz, 3H); Anal. calcd. for $C_{23}H_{28}O_4$ 74.97% C, 7.66% H. Found 74.75% C, 7.39% H.

3-(1,1-Dimethylheptyl)-1,9-dihydroxy-6H-dibenzo[b,d] pyran-6-one (5). 3-(1,1-Dimethylheptyl)-1-hydroxy-9-methoxy-6H-dibenzo[b,d]pyran-6-one (4b) (200 mg, 0.54 mmol) was dissolved in 12 mL of dry dichloromethane, 2 mL of a 1M solution of boron tribromide in dichloromethane (2 mmol) was added and the resulting mixture was stirred at room temperature for 3 days. Water was added and the mixture was extracted with diethyl ether. The organic extract was dried and rotary evaporated. The residue was chromatographed on silica gel (50% ethyl ether-petroleum ether) to afford 150 mg of a flaky off-white foam: m.p. 103-108° C.; $R_f$: 0.28 (50% diethyl ether-petroleum ether); $^1$H NMR δ 8.60 (m, 1H), 8.35 (d, 1H), 7.05 (d, 1H), 6.90 (s, 1H), 6.73 (s, 1H), 6.10 (br s, 2H), 1.70-0.98 (series of m, 10H), 1.27 (s, 6H), 0.82 (t, J=6.6 Hz, 3H); Anal. calcd. for $C_{23}H_{28}O_4$ 74.55% C, 7.39% H. Found 72.70% C, 7.25% H.

3-(1,1-Dimethylheptyl)-9-methoxy-6,6-trimethyl-6H-dibenzo[b,d]pyran-1-ol (6b). As described above, starting from 3-(1,1-dimethylheptyl)-1-hydroxy-9-methoxy-6H-dibenzo[b,d]pyran-6-one (4b) (30 mg, 0.082 mmol) was obtained 25.7 mg (82%) of the title compound as a viscous oil. $R_f$: 0.22 (10% diethyl ether-petroleum ether); $^1$H NMR δ 7.72 (m, 1H), 7.15 (m, 1H), 6.80 (m, 1H), 6.57 (d, 1H), 6.40 (d, 1H), 5.20 (s, 1H), 3.83 (s, 3H), 1.59 (s, 6H), 1.71-1.10 (complex m, 11H), 1.23 (s, 6H), 0.82 (t, J=6.7 Hz, 3H); HRMS calcd. for $C_{25}H_{34}O_3$ 382.5357. Found 382.5361.

Single-Crystal X-Ray Diffraction Analysis of 4a and 4b

Analogue 4b $C_{23}H_{28}O_4$, F.W.=368.45, triclinic space group, a=6.768(2), b=8.794(3), c=17.880(5) Å, a=96.68(2), b=99.74(1), g=92.50(2)_, V=1039.5(5) Å$^3$, Z=2, $r_{calc}$=1.177 mg mm$^{-3}$, I(Cu Ka)=1.54178 Å, m=0.635 mm$^{-1}$, F(000) =396, T=295° K. The following parameters are common to (4a) and (4b) and where different they are indicated by enclosure in brackets.

A clear colorless 0.80×0.36×0.10 [0.48×0.21×0.14] mm crystal was used for data collection on an automated Bruker P4 diffractometer equipped with an incident beam monochromator. Lattice parameters were determined from 40[34] centered reflections within 7<2q<50_[6<2q<56_]. The data collection range had a {(sin q)/I}$_{max}$=0.55. Three standards, monitored after every 97 reflections, exhibited random variations with devs. up to ±2.5 [1.9]% during the data collection. A set of 3067 [3088] reflections was collected in the q/2q scan mode, and w scan rate (a function of count rate) from 7.5_/ min. to 30.0_/min. There were 2739 [2767] unique reflections. Corrections were applied for Lorentz, polarization, and absorption effects. The structure was solved with SHELXTL and refined with the aid of the SHELX97 system of programs. The full-matrix least-squares refinement on $F^2$ varied 312 [248] parameters: atom coordinates and anisotropic thermal parameters for all non-H atoms. H atoms were included using a riding model [coordinate shifts of C applied to attached H atoms, C—H distances set to 0.96 to 0.93 Å, H angles idealized, $U_{iso}(H)$ were set to 1.2 to 1.5 $U_{eq}(C)$. Final residuals were R 1=0.087 [0.086] for the 1572[2045] observed data with $F_o>4s(F_o)$ and 0.138[0.107] for all data. Final difference Fourier excursions of 0.20 and −0.29 [0.40 and −0.27]e Å$^{-3}$.

In 4a the hydrocarbon chain group is disordered such that the atoms may be located on an alternate position along the chain with occupancies of 0.62 and 0.38 for the major and minor positions. There is evidence that 4b is also disordered but the disorder could not be modeled with only a major and minor form. Tables of coordinates, bond distances and bond angles, and anisotropic thermal parameters, have been deposited with the Crystallographic Data Centre, Cambridge, CB2, 1EW, England.

Cannabinoid Mediated Antinociception.

Method. Male Sprague-Dawley rats (Harlan; Indianapolis, Ind.) 200-300 grams at time of testing, were maintained in a climate-controlled room on a 12-h light/dark cycle (lights on at 06:00 h) and food and water were available ad libitum. All of the testing was performed in accordance with the policies and recommendations of the International Association for the Study of Pain (IASP) and the National Institutes of Health (NIH) guidelines for the handling and use of laboratory animals and received approval from the Institutional Animal Care and Use Committee (IACUC) of the University of Arizona.

Figure 2:
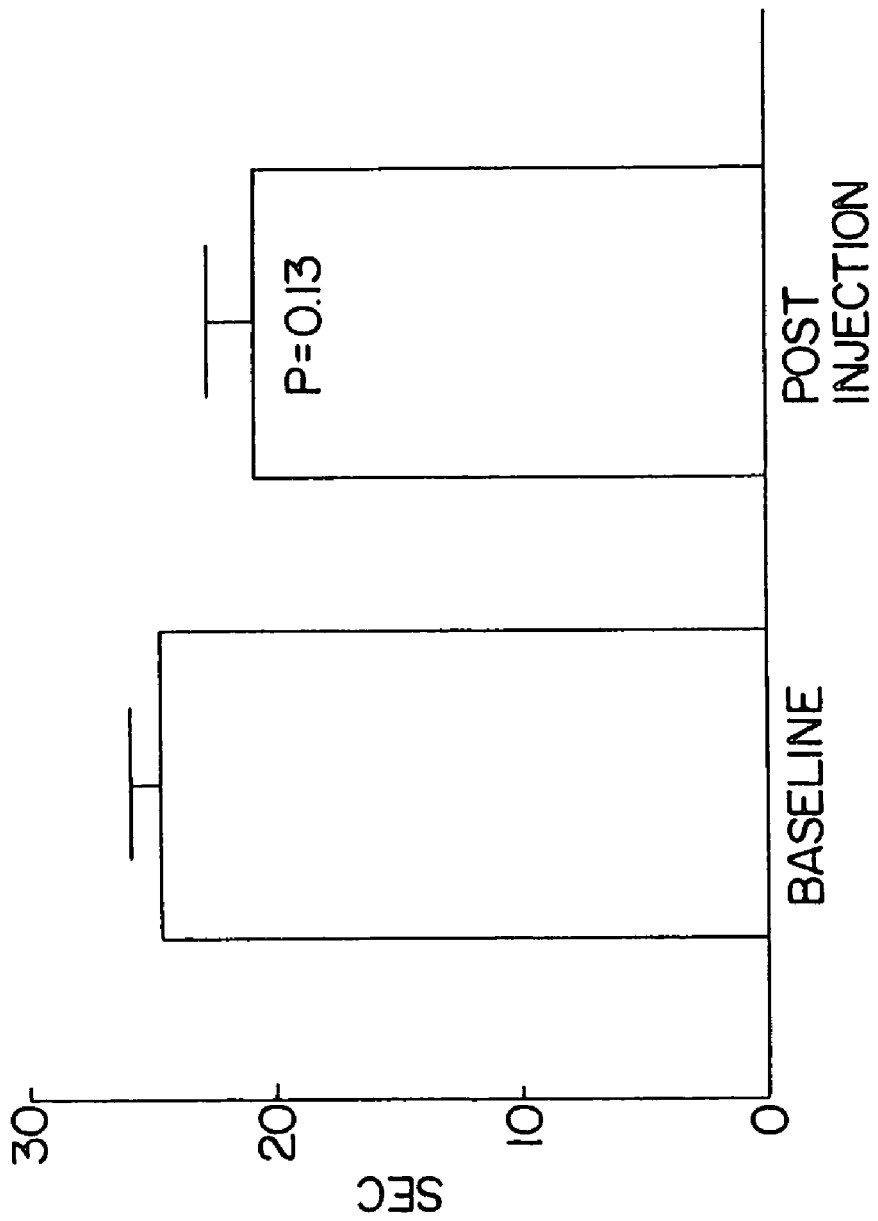
Figure 3:
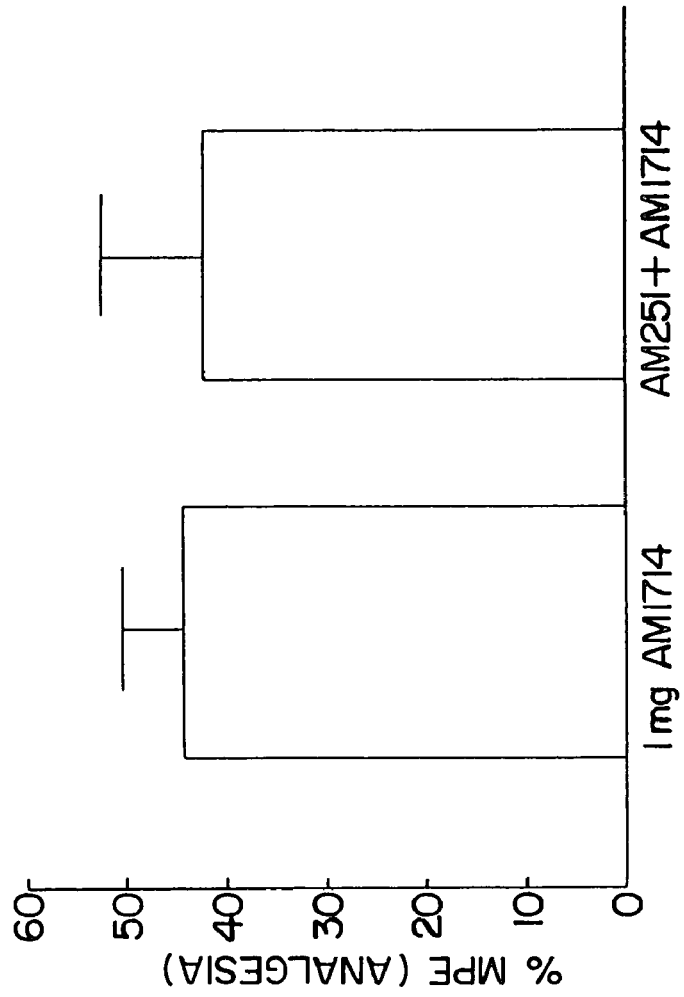
Figure 4:
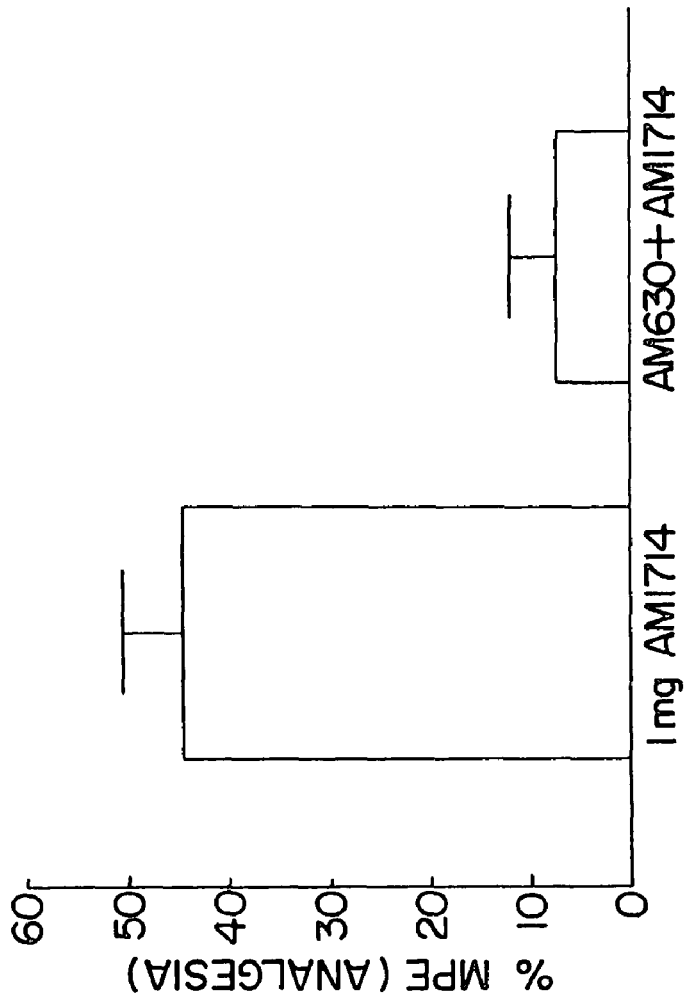
Figure 5:
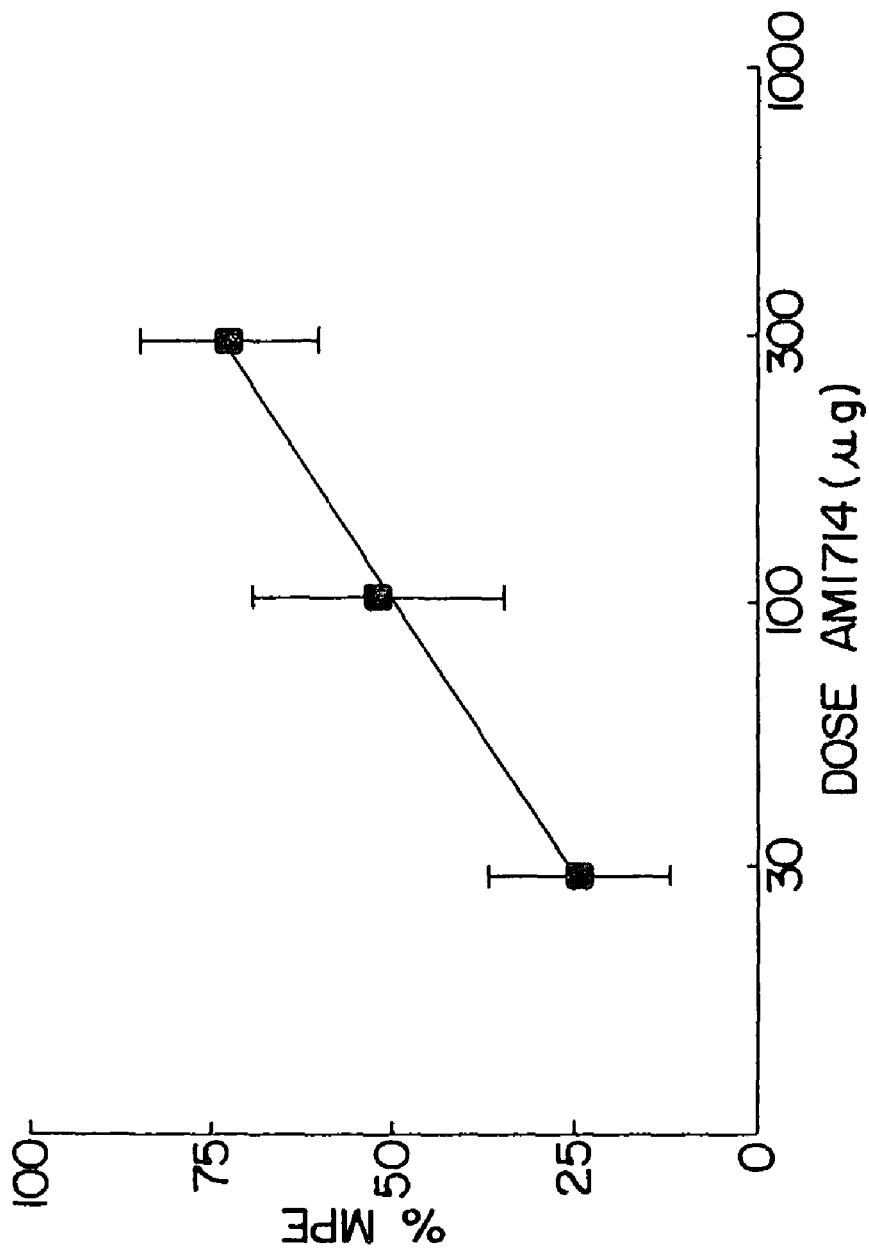
Figure 6:
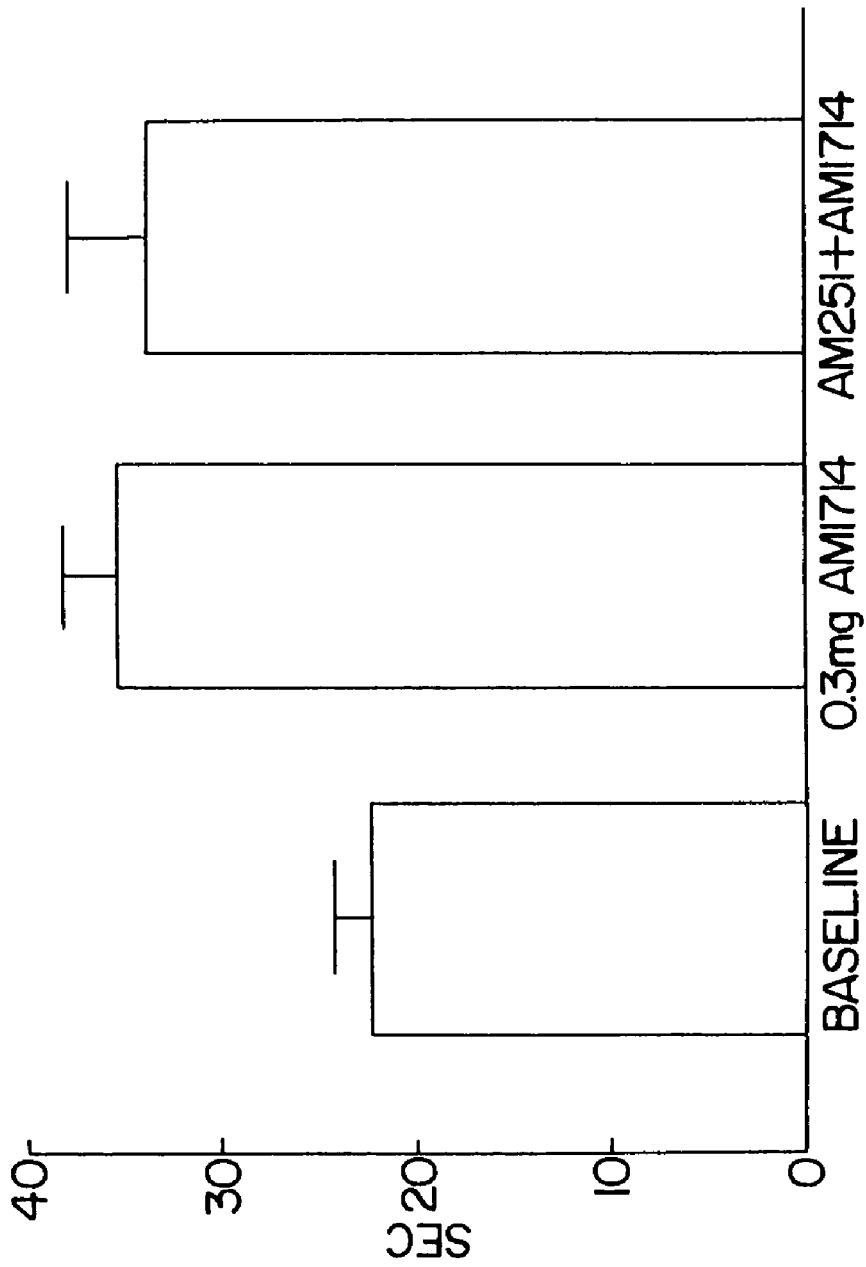
Figure 7:
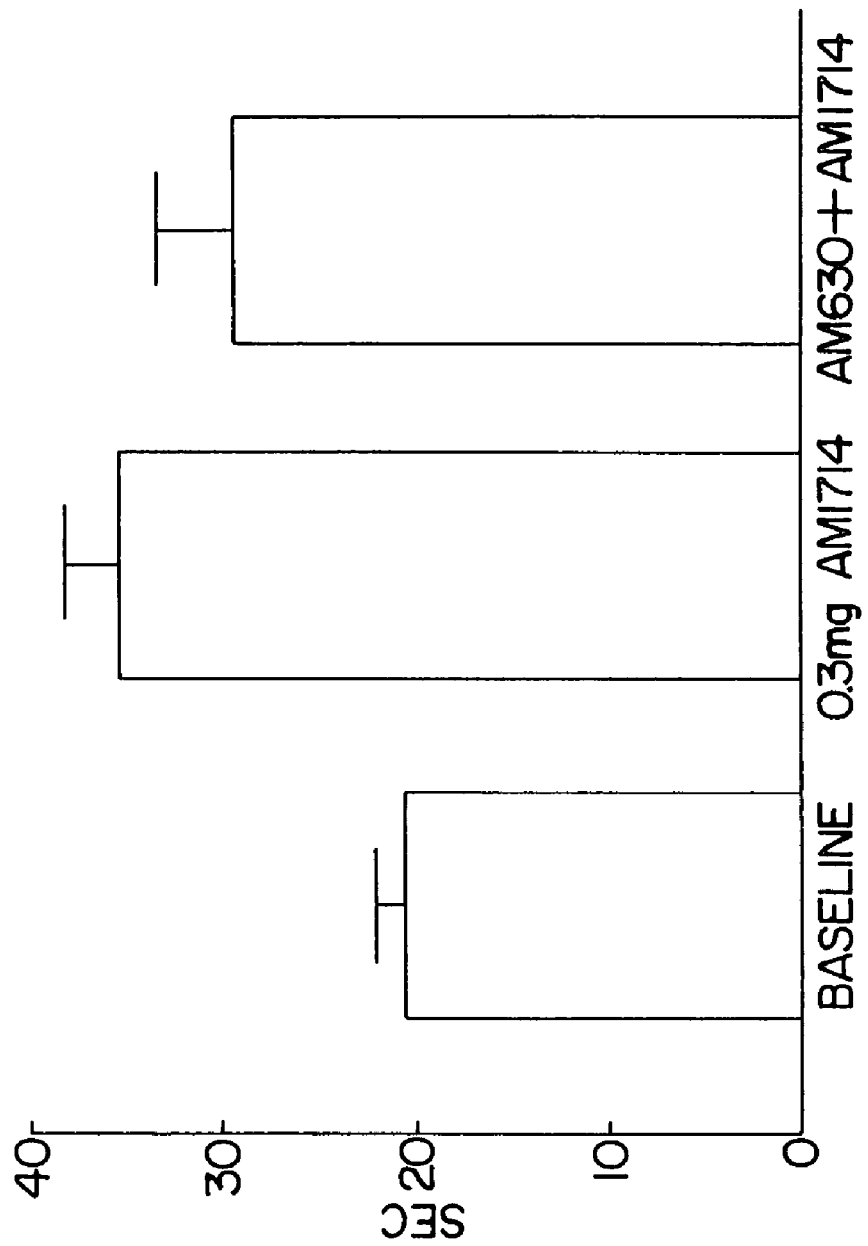
Figure 8:
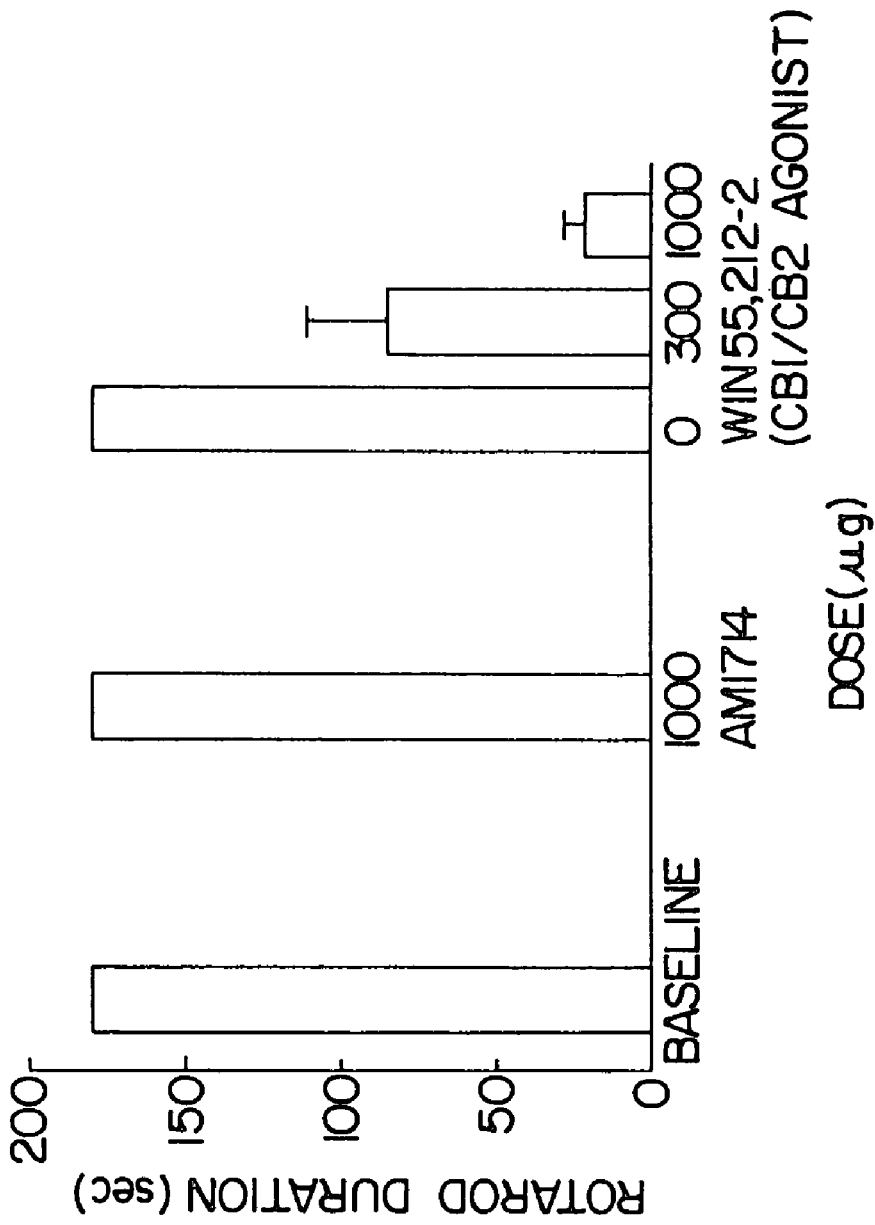
Figure 9:
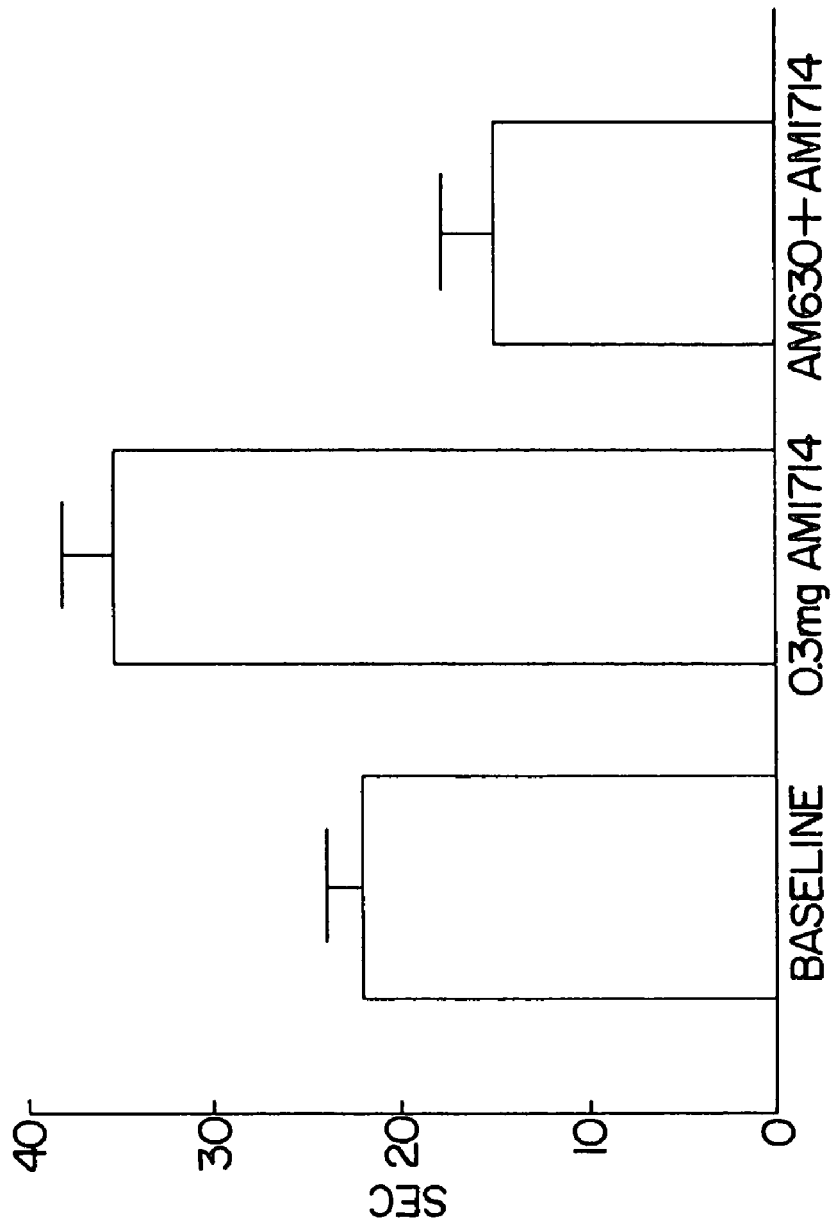
Figure 10:
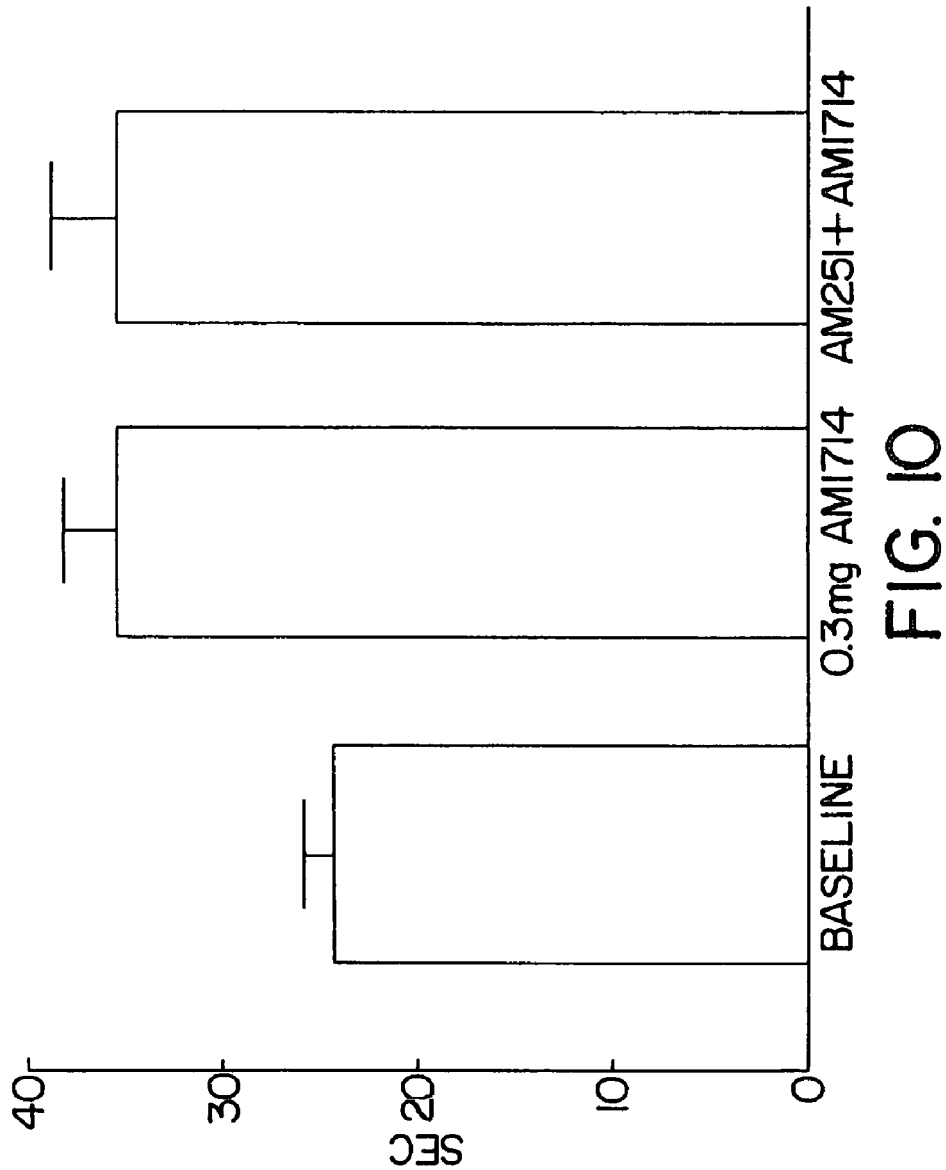
Figure 11:
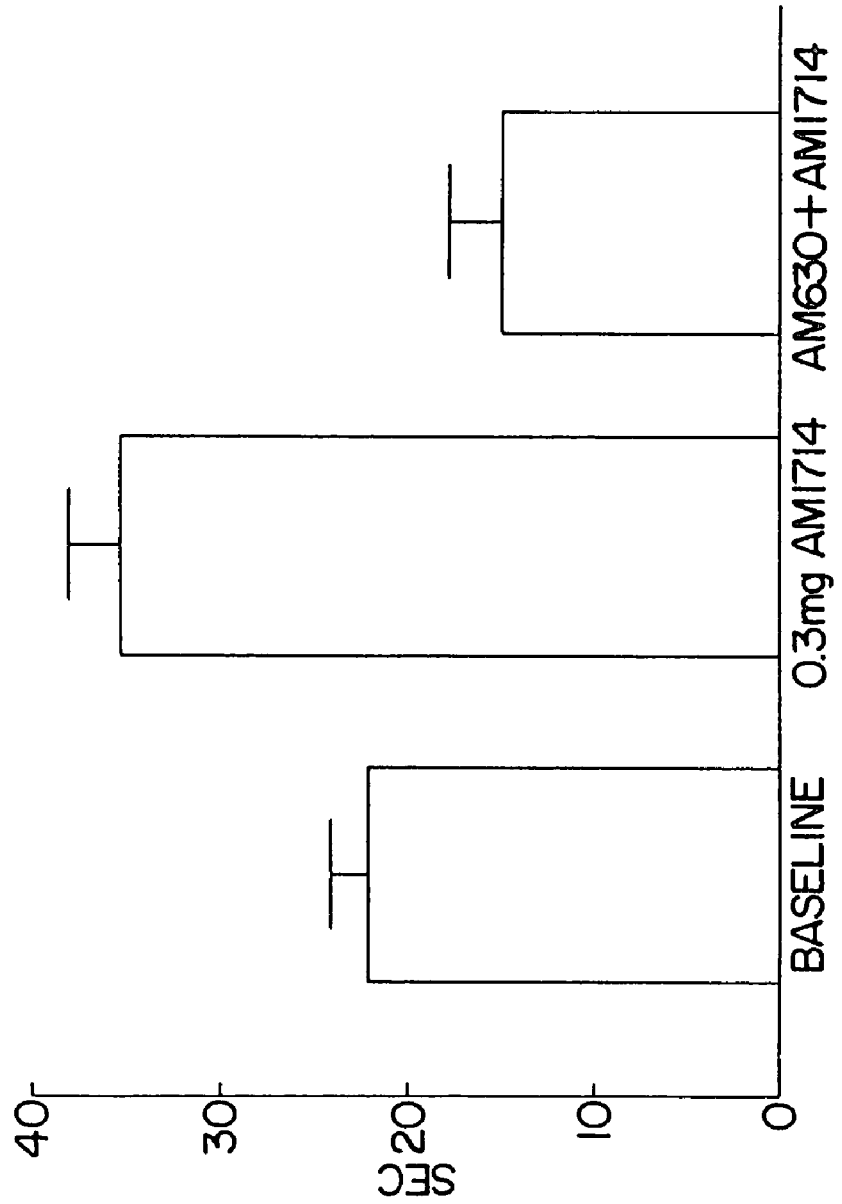
Figure 12:
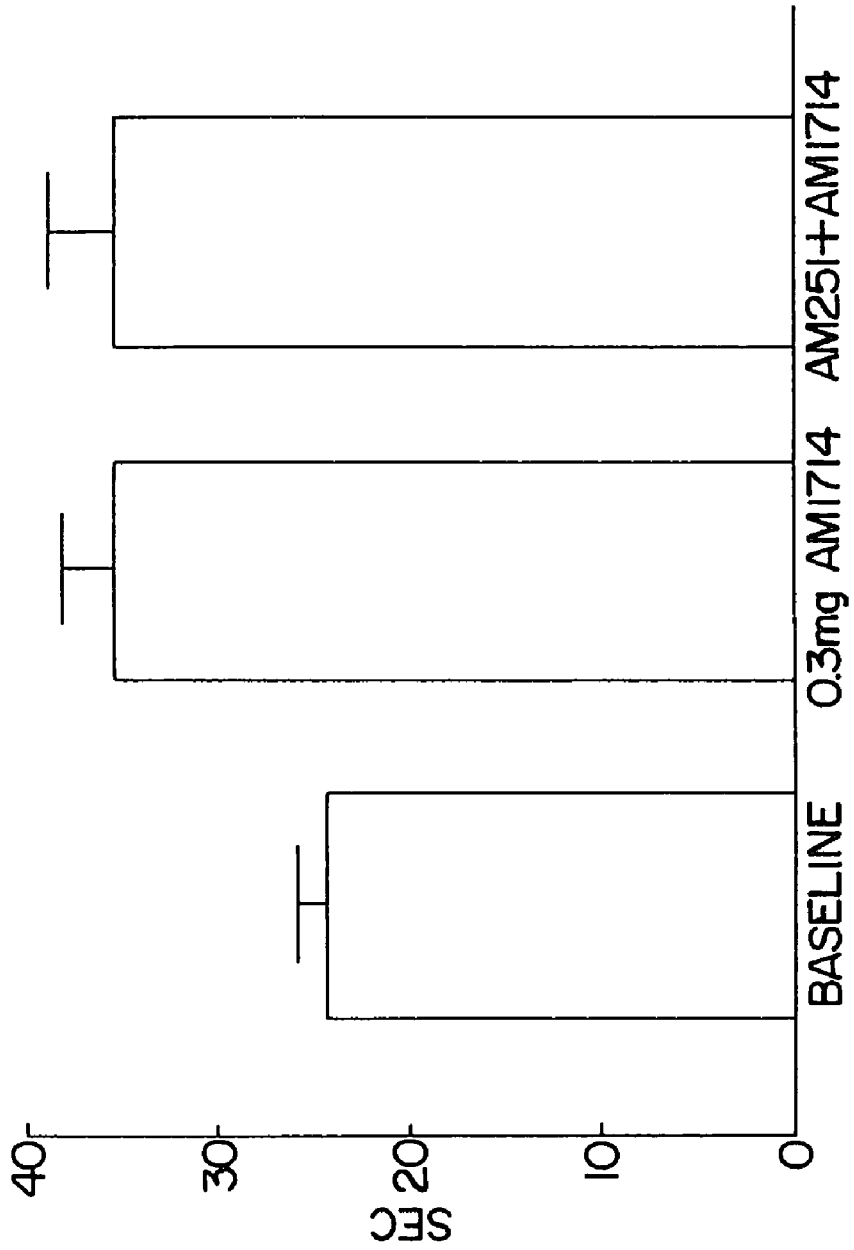
Figure 13:
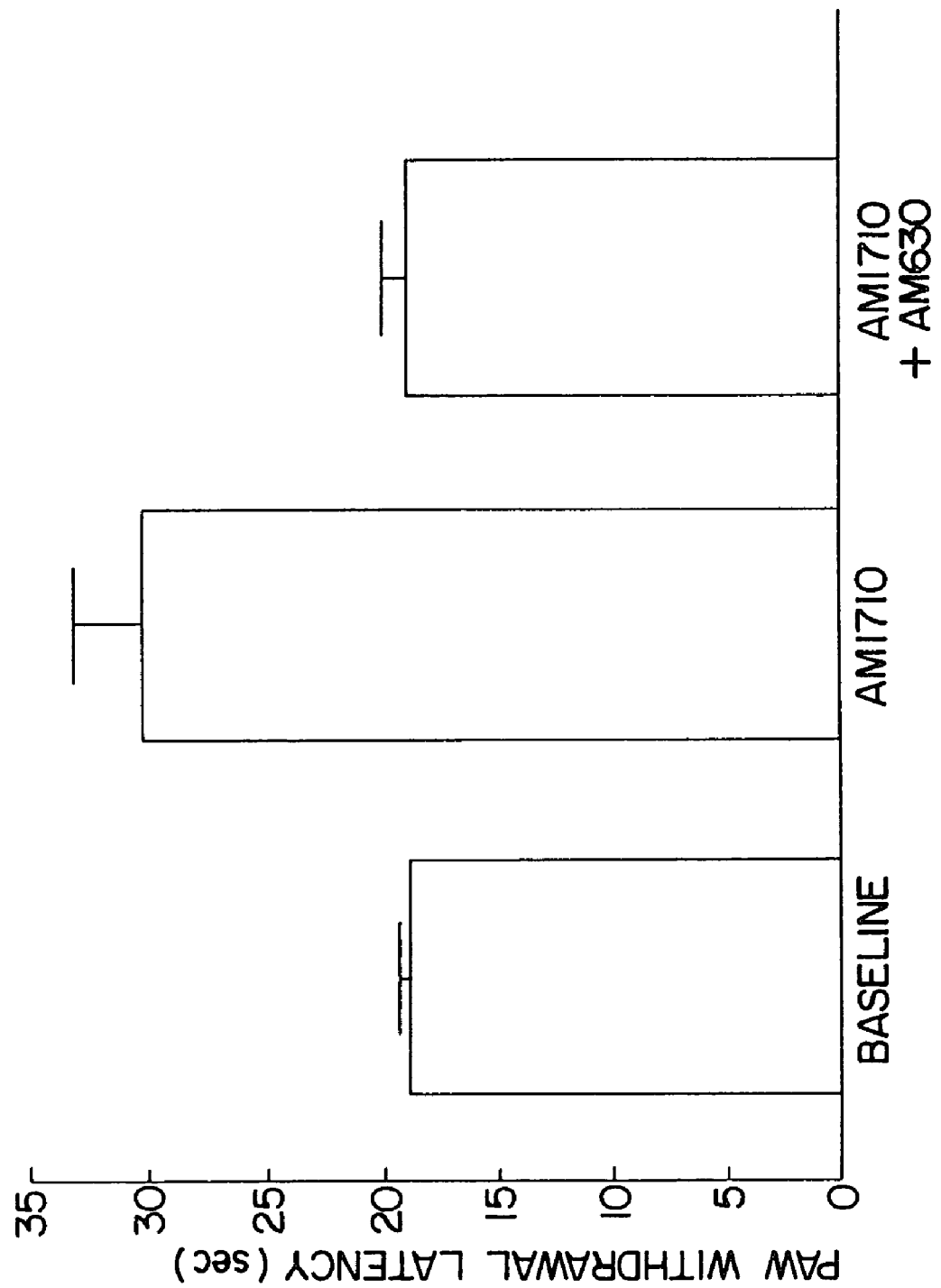

All drugs were dissolved in dimethyl sulfoxide (DMSO) and were injected subcutaneously in the plantar surface of the hindpaw in a total volume of 50 µl. DMSO given in hindpaw at this volume had no effect. The method of Hargreaves, K.; Dubner, R.; Brown, F.; Flores, C.; and Joris, J., *A New Sensitive Method for Measuring Thermal Nociception in Cutaneous Hyperalgesia. Pain,* 1988, 32, 77-88, the disclosure of which is hereby incorporated by reference, was employed to assess paw-withdrawal latency to a thermal nociceptive stimulus. Rats were allowed to acclimate within Plexiglas enclosures on a clear glass plate maintained at 30° C. A radiant heat source (i.e., high intensity projector lamp) was activated with a timer and focused onto the plantar surface of the hindpaw. Paw-withdrawal latency was determined by a photocell that halted both lamp and timer when the paw was withdrawn. The latency to withdrawal of the paw from the radiant heat source was determined both before and after drug or vehicle administration. A maximal cut-off of 40 sec was employed to prevent tissue damage. As shown in FIGS. 1-13, administration of compound AM1714 produced notable physiological effects in test animals including analgesia.

Materials AM1710 and AM1714 were tested for CB2 receptor binding affinity and for CB1 receptor affinity (to determine selectivity for the CB2 receptor). As used herein, "binding affinity" is represented by the $IC_{50}$ value which is the concentration of an analog required to occupy the 50% of the total number (Bmax) of the receptors. The lower the $IC_{50}$ value, the higher the binding affinity. As used herein an analog is said to have "binding selectivity" if it has higher binding affinity for one receptor compared to the other receptor; e.g. a cannabinoid analog which has an $IC_{50}$ of 0.1 nM for CB1 and 10 nM for CB2, is 100 times more selective for the CB1 receptor. The binding affinities ($K_i$) are expressed in nanomoles (nM).

For the CB1 receptor binding studies, membranes were prepared from rat forebrain membranes according to the procedure of P. R. Dodd et al, *A Rapid Method for Preparing Synaptosomes: Comparison with Alternative Procedures,* Brain Res., 107-118 (1981). The binding of the novel analogues to the CB1 cannabinoid receptor was assessed as described in W. A. Devane et al, *Determination and Characterization of a Cannabinoid Receptor in a Rat Brain,* Mol. Pharmacol., 34, 605-613 (1988) and A. Charalambous et al, *5'-azido Δ$^8$-THC: A Novel Photoaffinity Label for the Cannabinoid Receptor,* J. Med. Chem., 35, 3076-3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 Φg of membranes were incubated in silanized 96-well microtiter plate with TME containing 0.1% essentially fatty acid-free bovine serum albumin (BSA), 0.8 nM [$^3$H] CP-55,940, and various concentrations of test materials at 200° C. for 1 hour. The samples were filtered using Packard Filtermate 196 and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the using the assumptions of Cheng et al, *Relationship Between the Inhibition Constant ($K_i$) and the concentration of Inhibitor which causes 50% Inhibition ($IC_{50}$) of an Enzymatic Reaction,* Biochem. Pharmacol., 22, 3099-3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures,* Brain Res., 226, 107-118 (1981) which is incorporated by reference herein. Silanized centrifuge tubes were used throughout to minimize receptor loss due to adsorption. The CB2 binding assay was conducted in the same manner as for the CB1 binding assay. The binding affinities ($K_i$) were also expressed in nanomoles (nM).

AM1710 exhibited a CB2 affinity of 0.49 nM and about a 750-fold CB2 selectivity over CB1. Other cannabinoid analogs have been reported that show some selectivity for the CB2 receptor. However the inventive analogs described herein have a surprisingly high selectivity for the CB2 receptor that is higher than known analogs.

The physiological and therapeutic advantages of the inventive materials can be seen from the above disclosure and also with additional reference to the following references, the disclosures of which are hereby incorporated by reference. Arnone M., Maruani J., Chaperon P, et al, *Selective inhibition of sucrose and ethanol intake by SR141716, an antagonist of central cannabinoid (CB1) receptors*, Psychopharmacal, (1997) 132, 104-106. Colombo G, Agabio R, Diaz G. et al: *Appetite suppression and weight loss after the cannabinoid antagonist* SR141716. Life Sci. (1998) 63-PL13-PL117. Simiand J, Keane M, Keane P E, Soubrie P: SR 141716, *A CB1 cannabinoid receptor antagonist, selectively reduces sweet food intake in marmoset*. Behav. Pharmacol (1998) 9:179-181. Brotchie J M: *Adjuncts to dopamine replacement a pragmatic approach to reducing the problem of dyskinesia in Parkinson's disease*. Mov. Disord. (1998) 13:871-876. Terranova J-P, Storme J-J Lafon N et al: *Improvement of memory in rodents by the selective CB1 cannabinoid receptor antagonist*, SR 141716. Psycho-pharmacol (1996) 126:165-172. Hampson A L Grimaldi M. Axpirod J. Wink D: *Cannabidiol and (-) $\Delta^9$ tetrahydrocannabinol are neuroprotective antioxidants*. Proc. Natl Acad Sci. USA (1998) 9S:8268-8273. Buckley N E, McCoy K I, Mpzey E et al *Immunomodulation by cannabinoids is absent in mice deficient for the cannabinoid $CB_2$ receptor*. Eur. J Pharmacol (2000) 396:141-149. Morgan Dr: *Therapeutic Uses of Cannabis*. Harwood Academic Publishers, Amsterdam. (1997). Joy J E, Wagtson S J, Benson J A: *Marijuana and Medicine Assessing the Science Base*. National Academy Press, Washington, D.C., USA (1999). Shen M. Thayer S A: *Cannabinoid receptor agonists protect cultured rat hippocampal neurons from excitotoxicity*. Mol. Pharmacol (1996) 54:459-462. DePetrocellis L, Melck D, Palmisano A. et al: *The endogenous cannabinoid anandamide inhibits human breast cancer cell proliferation*. Proc Natl. Acad. Sci USA (1998) 95:8375-8380. Green K. *Marijuana smoking vs. cannabinoids for glaucoma therapy*. Arch. Ophibalmol. (1998) February 433-1437. Hemming M, Yellowlees P M, *Effective treatment of Tourette's syndrome with marijuana*. J. Psychopharmacol, (1993) 7:389-391. Muller-Vahl K B, Schneider U, Kolbe H, Emrich, H M. *Treatment of Tourette's syndrome with delta-9-tetrahydrocannabinol*. Am. J. Psychiat. (1999) 156-195. Muller-Vahl K B, Kolbe H, Schneider U, Emrich, H M *Cannabis in movement disorders*. Porsch. Kompicmentarmed (1999) 6 (suppl. 3) 23-27. Consroe P, Musty R, Rein J, Tillery W, Pertwee R. *The perceived effects of smoked cannabis on patents with multiple sclerosis*, Eur. Neurol. (1997) 38-44-48. Pinnegan-Ling D, Musty R. *Marinol and phantom limb pain: a case study*. Proc Inv. Cannabinoid Rea. Sec. (1994):53. Brenneisen R, Pgli A, Elsohly M A, Henn V. Spiess Y: *The effect of orally and rectally administered $\Delta^{9-}$tetrahydrocannabinol on spasticity, a pilot study with 2 patients*. Int. J. Clin Pharmacol Ther. (1996) 34:446-452. Martyn C N. Illis L S, Thom J. *Nabilone in the treatment of multiple sclerosis*. Lancet (1995) 345:579. Maurer M, Henn V, Dittrich A, Hofmann A. *Delta-9-tetrahydrocannabinol shows antispastic and analgesic effects in a single case double-blind trial*. Eur. Arch. Psychiat. Clin. Neurosci. (1990), Z40:1-4. Herzberg U, Eliav E, Bennett G J, Kopin I J: *The analgesic effects of R(+) WIN 55,212-2 mesylate, a high affinity cannabinoid agonist in a rare model of neuropathic pain*. Neurosci. Letts. (1997) 221:157-160. Richardson J D, Kilo S. Hargreaves K M, *Cannabinoids reduce dryperalgesia and inflammation via interaction with peripheral CB1 receptors*. Pain (1998) 75:111-119. Ricardson J D, Aanonsen I, Hargreaves K M: *Antihyperalgesic effects of a spinal cannabinoids*. Eur. J. Pharmacol. (1998) 346:145-153. Calignano A, La Rana G. Diuffrida A, Piomelli D: *Control of pain initiation by endogenous cannabinoids*. Nature (1998) 394:277-291. Wagner J A, Varga K, Jarai Z, Kunos G: *Mesenteric vasodilation mediated by endothelia anandamide receptors*. Hypertension (1999) 33:429-434. Schuel, H., Burkman, L. J., Picone, R. P., Bo, T., Makriyannis, A., *Cannabinoid receptors in human sperm*. Mol. Biol. Cell., (1997) (8), 325a.

The inventive analogs described herein, and physiologically acceptable salts thereof, have high potential when administered in therapeutically effective amounts for providing a physiological effect useful to treat pain, peripheral pain, glaucoma, epilepsy, nausea such as associated with cancer chemotherapy, cancer, neurodegenerative diseases including Multiple Sclerosis, Parkinson's Disease, Huntington's Chorea and Alzheimer's Disease, to reduce fertility; to prevent or reduce diseases associated with motor function such as Tourette's syndrome; to prevent or reduce inflammation; to provide neuroprotection and to modulate the immune system. Thus, another aspect of the invention is the administration of a therapeutically effective amount of an inventive compound, or a physiologically acceptable salt thereof, to an individual or animal to provide a physiological effect.

Those skilled in the art will recognize, or be able to ascertain with no more than routine experimentation, many equivalents to the specific embodiments of the invention disclosed herein. Such equivalents are intended to be encompassed by the scope of the invention.

What is claimed is:

1. A method of selectively stimulating the CB2 receptors in an individual or animal comprising administering to the individual or animal a therapeutically effective amount of a compound having the formula:

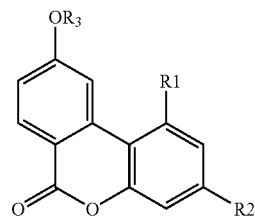

and physiologically acceptable salts thereof, wherein
$R_1$ is selected from OH; H; $OCH_3$; $N_3$; $NH_2$; $O(CH_2)_nN(CH_3)_2$ and

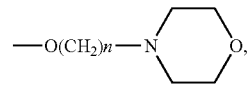

where n is an integer from 1-3;
$R_2$ is selected from $(CH_2)_nCH_3$, where n is an integer from 4-6;
$C(CH_3)_2(CH_2)_nCH_3$, where n is an integer from 3-5;

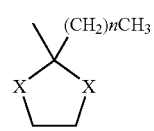

where each X is independently selected from $CH_2$, O, S and NH and n is an integer from 3-5;
$(CH_2)_nC\equiv CH$ where n is an integer from about 3-5;
$C\equiv C(CH_2)_nCH_3$ where n is an integer from 2-4 and

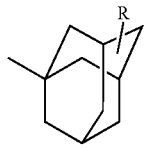

where R is H, $(CH_2)_nCH_3$, and n is a maximum of 7;
$R_3$ is selected from H; $CH_3$; $C_2H_5$; $C_3H_7$; $C_4H_9$; $(CH_2)_nN(CH_3)_2$ and

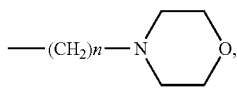

where n is an integer from 1-3;
with the proviso that if $R_1$ is H or OH and $R_3$ is selected from H; $CH_3$ and $C_2H_5$, than $R_2$ can not be

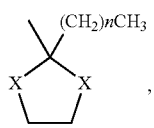

where each X is independently selected from $CH_2$, O, S and NH and n is an integer from 3-5, or

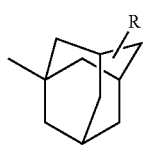

where R is H, $(CH_2)_nCH_3$, and n is a maximum of 7.

2. The method of claim 1, wherein:
$R_1$ is selected from H; $OCH_3$; $N_3$; $NH_2$; $O(CH_2)N(CH_3)_2$ and

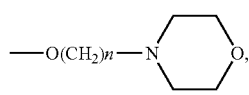

where n is an integer from 1-3;
$R_2$ is selected from $(CH_2)_nCH_3$, where n is an integer from 4-6;
$C(CH_3)_2(CH_2)_nCH_3$, where n is an integer from 3-5;

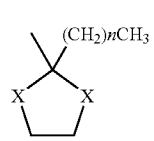

where each X is independently selected from $CH_2$, O, S and NH and n is an integer from 3-5;
$(CH_2)_nC\equiv CH$ where n is an integer from about 3-5;
$C\equiv C(CH_2)_nCH_3$ where n is an integer from 2-4 and

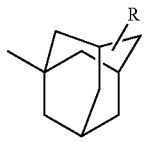

where R is H, $(CH_2)_nCH_3$, and n is a maximum of 7; and
$R_3$ is selected from H; $CH_3$; $C_2H_5$; $C_3H_7$; $C_4H_9$; $(CH_2)_nN(CH_3)_2$ and

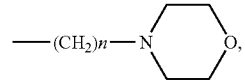

where n is an integer from 1-3.

3. The method of claim 1, wherein:
$R_1$ is selected from H; OH; $OCH_3$; $N_3$; $NH_2$; $O(CH_2)_nN(CH_3)_2$ and

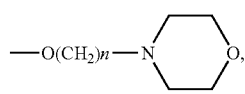

where n is an integer from 1-3;
$R_2$ is selected from $(CH_2)_nCH_3$, where n is an integer from 4-6;
$C(CH_3)_2(CH_2)_nCH_3$, where n is an integer from 3-5;

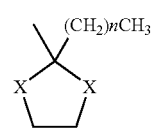

where each X is independently selected from $CH_2$, O, S and NH and n is an integer from 3-5;
$(CH_2)_nC\equiv CH$ where n is an integer from about 3-5;
$C\equiv C(CH_2)_nCH_3$ where n is an integer from 2-4 and

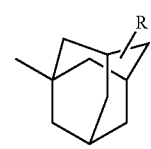

where R is H, $(CH_2)_nCH_3$, and n is a maximum of 7; and
$R_3$ is selected from $C_3H_7$; $C_4H_9$; $(CH_2)_nN(CH_3)_2$ and

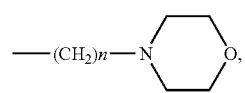

where n is an integer from 1-3.

4. The method of claim 1, wherein:
$R_1$ is selected from H; OH; $OCH_3$; $N_3$; $NH_2$; $O(CH_2)_nN(CH_3)_2$ and

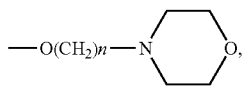

where n is an integer from 1-3;
$R_2$ is selected from $(CH_2)_nCH_3$, where n is an integer from 4-6;
$C(CH_3)_2(CH_2)_nCH_3$, where n is an integer from 3-5;
$(CH_2)_nC\equiv CH$ where n is an integer from about 3-5; and
$C\equiv C(CH_2)_nCH_3$ where n is an integer from 2-4; and
$R_3$ is selected from H; $OH_3$; $C_2H_5$; $C_3H_7$; $C_4H_9$; $(CH_2)_nN(CH_3)_2$ and

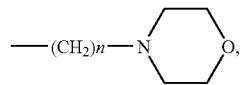

where n is an integer from 1-3.

5. The method of claim 1 of selectively stimulating the CB2 receptors in an individual or animal for providing a physiological effect to treat a condition selected from at least one of central pain, peripheral pain, inflammatory pain, pain associated with cancer chemotherapy, neuropathy, Multiple Sclerosis, Parkinson's Disease, Huntington's Chorea, Alzheimer's Disease, Amyotrophic Lateral Sclerosis, and inflammation comprising administering to the individual or animal a therapeutically effective amount of a compound of claim 1 or a physiologically acceptable salt thereof.

6. The method of claim 1 of selectively stimulating the CB2 receptors in an individual or animal for providing a physiological effect to treat a condition selected from at least one of pain and peripheral pain, comprising administering to the individual or animal a therapeutically effective amount of a compound of claim 1 or a physiologically acceptable salt thereof.

* * * * *

UNITED STATES PATENT AND TRADEMARK OFFICE
CERTIFICATE OF CORRECTION

PATENT NO. : 7,741,365 B2  
APPLICATION NO. : 11/323560  
DATED : June 22, 2010  
INVENTOR(S) : Makriyannis et al.

Page 1 of 1

It is certified that error appears in the above-identified patent and that said Letters Patent is hereby corrected as shown below:

Column 13:  
Line 43, delete "$O(CH_2)N(CH_3)_2$" and substitute --$O(CH_2)_nN(CH_3)_2$--.

Column 15:  
Line 13, delete "$OH_3$" and substitute --$CH_3$--.

Signed and Sealed this

Nineteenth Day of October, 2010

David J. Kappos  
*Director of the United States Patent and Trademark Office*